(12) United States Patent
Widjajana et al.

(10) Patent No.: US 11,229,611 B2
(45) Date of Patent: Jan. 25, 2022

(54) CLOBAZAM TRANSDERMAL DELIVERY SYSTEM AND USES THEREOF

(71) Applicant: TAHO Pharmaceuticals Ltd., Taipei (TW)

(72) Inventors: Moonika Sari Widjajana, Keelung (TW); Tachien Lu, New Taipei (TW); Catherine Lee, Happy Valley, OR (US)

(73) Assignee: TAHO PHARMACEUTICALS LTD., Taipei (TW)

( * ) Notice: Subject to any disclaimer, the term of this patent is extended or adjusted under 35 U.S.C. 154(b) by 0 days.

(21) Appl. No.: 17/238,327

(22) Filed: Apr. 23, 2021

(65) Prior Publication Data
US 2021/0338600 A1 Nov. 4, 2021

Related U.S. Application Data

(60) Provisional application No. 63/017,841, filed on Apr. 30, 2020.

(51) Int. Cl.

| | | |
|---|---|---|
| *A61K 9/70* | (2006.01) | |
| *A61K 31/5513* | (2006.01) | |
| *A61K 9/107* | (2006.01) | |
| *A61K 47/10* | (2017.01) | |
| *A61K 47/26* | (2006.01) | |
| *A61K 47/12* | (2006.01) | |
| *A61K 47/32* | (2006.01) | |
| *A61K 47/44* | (2017.01) | |
| *A61K 47/20* | (2006.01) | |
| *A61K 47/14* | (2017.01) | |

(52) U.S. Cl.
CPC .......... *A61K 9/7084* (2013.01); *A61K 9/1075* (2013.01); *A61K 31/5513* (2013.01); *A61K 47/10* (2013.01); *A61K 47/12* (2013.01); *A61K 47/14* (2013.01); *A61K 47/20* (2013.01); *A61K 47/26* (2013.01); *A61K 47/32* (2013.01); *A61K 47/44* (2013.01)

(58) Field of Classification Search
None
See application file for complete search history.

(56) References Cited

U.S. PATENT DOCUMENTS

| | | |
|---|---|---|
| 4,906,169 A | 3/1990 | Chien et al. |
| 4,951,622 A | 8/1990 | Takahashi et al. |
| 5,232,702 A | 8/1993 | Pfister et al. |
| 2004/0213832 A1 | 10/2004 | Venkatraman et al. |
| 2005/0266085 A1 | 12/2005 | Warner et al. |
| 2017/0049714 A1* | 2/2017 | Plakogiannis ....... A61K 9/7084 |
| 2018/0055789 A1 | 3/2018 | Farr et al. |
| 2020/0009154 A1 | 1/2020 | Plakogiannis et al. |

FOREIGN PATENT DOCUMENTS

| | | |
|---|---|---|
| WO | 2012135536 A1 | 10/2012 |
| WO | 2016069396 A2 | 5/2016 |

OTHER PUBLICATIONS

Ng et al. "Randomized, phase III study results of clobazam in Lennox-Gastaut syndrome", Neurology. Oct. 11, 2011;77(15):1473-81. doi: 10.1212/WNL.0b013e318232de76. Epub Sep. 28, 2011. PMID: 21956725. 12 pages.
Tolbert et al. "A Comprehensive Overview of the Clinical Pharmacokinetics of Clobazam", The Journal of Clinical Pharmacology. Aug. 10, 2018, 59 (1) 7-19. 13 pages.
Bonthagarala et al. "Formulation Development and Evaluation of Aceclofenac Microemulsion", Department of Pharmaceutics, SIMS College of Pharmacy, SIMS Group of Institutions, Mangaldas Nagar, Guntur, -522001, Andhra Pradesh, India. Aug. 1, 2016, 7(8): 1000-12. doi: 10.13040/IJPSR.0975-8232.7(8). 13 pages.
International Search Report and Written Opinion in corresponding International Patent Application No. PCT/US2021/028771 dated Jul. 16, 2021. 6 pages.

* cited by examiner

*Primary Examiner* — Nannette Holloman
(74) *Attorney, Agent, or Firm* — Leason Ellis LLP

(57) ABSTRACT

The present invention relates to transdermal drug delivery system of pharmaceutical compositions, which have a satisfactory in-vitro performance and good bioavailability. In particular, the transdermal pharmaceutical composition of clobazam in the present invention includes a micro-emulsion in liquid or semi solid form, in a dosage form adapted for transdermal delivery (e.g., transdermal patch) for treatment of certain types of epilepsy and anxiety for continues application.

20 Claims, 14 Drawing Sheets

CLOBAZAM TRANSDERMAL DELIVERY SYSTEM AND USES THEREOF

This application claims priority to U.S. provisional application Ser. No. 63/017,841 filed Apr. 30, 2020 which is incorporate by reference in its entirety.

1. FIELD

The present disclosure relates to a clobazam transdermal delivery system. More specifically, the present invention relates to a clobazam transdermal patch comprising a clobazam microemulsion for transdermal/topical administration, method of making and uses thereof.

2. BACKGROUND

Epilepsy is a group of neurological disorders characterized by epileptic seizures. These epileptic seizures are the result of excessive and abnormal cortical nerve cell activity in the brain, which causes episodes that can vary from brief and nearly undetectable to long periods of vigorous shaking. Lennox-Gastaut syndrome (LGS) is a form of severe epilepsy that begins in childhood. Multiple types of seizures and intellectual disability characterize it. The prognosis for individual with LGS varies. There is no cure for the disorder. Complete recovery, including freedom from seizures and normal development, is very unusual.

Lennox Gastaut Syndrome is one of the catastrophic childhood epilepsy syndromes, which is characterized by multiple seizure types including but not limited to tonic, atonic, atypical absence and generalized tonic-clonic seizures.

LGS develops during first decade of life, typically between 3-5 years of age and is common in males. The basic symptoms of it are multiple types of generalized seizures, difficult to control and/or slowness of intellectual growth such as mental retardation and behavioral problems. LGS is a severe epilepsy syndromes that are associated with refractory seizures, cognitive impairment, and increased risk of mortality related to seizures. Seven drugs (clobazam, rufinamide, topiramate, lamotrigine, felbamate, and clonazepam, Cannabidiol) are approved by FDA for reduction of seizures in patients with LGS. Despite the approved therapies most patients continue to have poorly-controlled seizures some drugs are poorly tolerated or have the potential for serious adverse events The prevalence of LGS in developed countries was approximately 2 per 100,000 children and in Europe 0.1-0.28 per 1000. Studies demonstrated that the figure of LGS is relatively consistent across the developed populations. In Atlanta, USA, LGS accounts for 4% of patients with childhood epilepsy, with a reported incidence of 0.26 per 1000 live birth.

Clobazam is a newer 1,5-benzodiazepine that is better tolerated and effective for all seizure types including drop attack for LGS. Clobazam is a benzodiazepine, which acts to enhance the actions of inhibitory neurons in the brain. This is accomplished by binding to certain sites on neuronal GABA-A1 receptors in a manner that enhances their efficacy. Since GABA is the principle inhibitory neurotransmitter in the brain, the actions of benzodiazepines are to reduce neuronal activity, reduce anxiety, promote sedation, and prevent the uncontrolled spread of neural excitation that result in epileptic seizures. Clobazam is class IV controlled substance because benzodiazepines can induce drug dependence.

Clobazam was first approved in 1970 in Australia (international birth date) and has also been approved for the treatment of anxiety and/or the adjunctive treatment of epilepsy in over 100 countries. It is one of the latest drug to be approved by the FDA for the treatment of seizures associated with LGS. No other medications approved by the FDA have demonstrated the degree of efficacy that has been noted with clobazam use (frequently 0.50% reduction in DS). The decrease in DS with clobazam compared to other seizure types is particularly robust, and is primarily responsible for the cost-effectiveness of the drug since use is expected to result in fewer seizure-related injuries.

Clobazam is used to treat CNS related disorders such as anxiety and epilepsy. The drug is currently sold as suspension and tablet form for oral administration.

Clobazam is used broadly across seizure types in territories outside of US. Medication adherence is a very important concern for prescribers since missing a single dose leads to increase in seizure frequency or severity. Many patients with LGS have dysphagia (difficulty swallowing) or use feeding tubes. Therefore, there is a need for alternative formulations of clobazam for the treatment of seizures. Because the side effects associated with administration of antiseizure medications can significantly impact a patient's health and well-being, alternatives to the current therapies are needed.

With respect to improved patient compliance, a transdermal patch is beneficial to patients in comparison to tablets or injectables. A patient can easily forget whether he or she has already taken a capsule or tablet whereas, in contrast, a patient can easily tell whether a new transdermal patch has been applied, making it easier for a patient to follow required dosing regimen. Dosing regimen compliance in the patients with seizure is particularly important since seizure is a neurological disease that requires lifelong treatment. Transdermal delivery system would therefore provide a needed alternative to oral formulation and will result in better compliance over twice daily oral formulation. Transdermal delivery system will also reduce the dosing frequency and GI side effects. It will also relief the burden on caregiver to administer LGS patients where difficulty swallowing and feeding tubes are common. Transdermal delivery of medication can easily be terminated where oral formulation does not provide this flexibility.

However, Clobazam faces many technology barriers to be formulated as a transdermal delivery system. First, it is a poor permeation candidate.

Second, it has poor water Solubility: 0.164 mg/mL. An effective daily dose of clobazam is about 20-40 mg.

US 2017/0049714, WO2017029567A1, and U.S. Pat. No. 10,624,901 B2 describes a transdermal drug delivery system (TDDS) for administration of clobazam comprising: an active substance area or reservoir comprises a pharmaceutical composition comprising clobazam and at least one excipient; an impermeable backing layer; optionally, a releasing membrane, which is covered by a detachable backing layer. However, it is a pouch system which might have leaking issues, and it cannot be cut or divided to adjust to the dose required.

There is a need for alternative formulations of clobazam which overcome the difficulties of oral formulations and which enhance patient compliance.

3. SUMMARY

The present invention relates to transdermal drug delivery system of pharmaceutical compositions, which have a satisfactory in-vitro performance and good bioavailability. In particular, the transdermal pharmaceutical composition of clobazam in the present invention includes a micro-emulsion in liquid or semi solid form, in a dosage form adapted for transdermal delivery (e.g., pressure sensitive transdermal patch) for treatment of certain types of epilepsy and anxiety for continued application.

Surprisingly, the present disclosure overcomes the challenges in formulation clobazam in transdermal delivery system. The present disclosure provides a transdermal drug delivery system of clobazam that overcomes the inherent technological barriers formulating this drug for transdermal delivery.

Provided herein is a transdermal drug delivery system comprising: (a) a drug-containing layer comprising (i) an oil-in-water microemulsion comprising: an oily phase comprising clobazam or a pharmaceutically acceptable salt thereof, an oily component and a solvent; and a hydrophilic phase comprising a surfactant, the microemulsion further comprising at least one of a permeation enhancer and/or a solubilizer; and (ii) an adhesive component comprising a first adhesive, wherein the adhesive component comprises between about 30% and less than about 50% of the drug-containing layer; and (b) an impermeable backing layer. In some embodiments, the transdermal drug delivery system is in the form of a transdermal patch.

In some embodiments, the ratio of the microemulsion component to the adhesive component is from about 90:10 to about 70:30 or from about 70:30 to about 60:40. In other embodiments, the ratio of the microemulsion component to the adhesive component is from about 10:90 to about 70:30 or from about 70:30 to about 51:49.

In certain embodiments, provided herein is a transdermal device comprising an impermeable backing layer. In certain embodiments, the transdermal device also comprises, optionally, a blocking layer where the drug has low or no solubility (this layer is to prevent drug permeate upwards). In certain embodiments, the transdermal device comprises one or more of the following:
   (i) silicone adhesive layer with or without drug;
   (ii) rubber adhesive layer with or without drug; or
   (iii) PIB layer with or without drug.
In certain embodiments, the transdermal device comprises one or more drug in adhesive layer:
   (i) Polymer matrix system combine with pressure sensitive adhesive system,
   (ii) Microemulsion with pressure sensitive adhesive system, where the microemulsion comprising an oil phase, a solvent and co-solvent phase, surfactant and co-surfactant phase and hydrophilic phase
   (iii) drug with enhancer in pressure sensitive adhesive system, or
   (iv) a hydrogel system
   Optionally, the transdermal device further comprises one or more of the following: a releasing membrane; a contact adhesive layer; or a release liner layer.

In certain embodiments, the oily component in the oily phase comprises one or more oils selected from the group consisting of aromatic oils, mineral oils, plant oils, animal oils, synthetic oils, silicone oils, fluoro oils, and any combination thereof. In one embodiment, the oil is 4-allyl-2-ethoxyphenol (2-Methoxy-4-(prop-2-en-1-yl) phenol).

In some non-limiting embodiments, the oily phase comprises 4-allyl-2-ethoxyphenol, levulinic acid, lactic acid, peg-6 caprylic/capric glycerides, pyruvic acid, and/or sodium lauryl sulfoacetate (and) disodium laureth sulfosuccinate.

In some non-limiting embodiments, the hydrophilic phase comprises benzyl alcohol, polyethylene glycol, ethyl levulinate, phenoxy ethanol, phenyl acetate, and/or triacetin.

In certain embodiments, the solvent is selected from the group consisting of C1-C20 alcohols, polyhydric alcohols, isopropyl myristate, glycols selected from the group consisting of propylene glycol, polyethylene glycol, dipropylene glycol and hexylene glycol; glycerine, imidazolidinones, 1,3-dimethyl-2-imidazolidinone (DMI), pyrrolidones selected from the group consisting of N-methyl 2-pyrrolidone (NMP), 2-pyrrolidone; sulfoxides selected from the group consisting of dimethyl sulfoxide and decyl methyl sulfoxide; dimethyl isosorbide, mineral oils, vegetable oils, and carboxylic acids selected from the group consisting of acrylic acid, lactic acid and acetic acid. In certain embodiments, the solvent comprises dimethyl sulfoxide (DMSO), 1,3-dimethyl-2-imidazolidinone (DMI), acrylic acid and/or NMP.

In certain embodiments, the surfactant is selected from the group consisting of an anionic surfactant, a cationic surfactant, a zwitterionic surfactant, a nonionic surfactant, and mixtures thereof. In some embodiments, may be selected from the group consisting of sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80 (Tween)), kolliphor derivates, sodium lauryl sulfate, sorbitan esters selected form the group consisting of sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate and sorbitan tri-isostearate, lecithin pharmaceutical acceptable salts thereof and combinations thereof.

In certain embodiments, the microemulsion comprises at least one excipient selected from the group consisting of alcohol, glycols, esters, ketones, and any combination thereof.

In certain embodiments, the microemulsion further comprises one or more excipients selected from the group consisting of alkyl benzoates, carboxylic acids, surfactants, emulsifiers, and any combination thereof.

In certain embodiments, the transdermal drug delivery system further comprises a crystallization inhibitor. In some non-limiting embodiments, the crystallization inhibitor may be selected from the group consisting of cellulose ethers, methyl cellulose ethers, cellulose, hydroxylated cellulose, methyl cellulose, and hydroxylated methyl cellulose, gums selected from guar, locust, karaya, xanthan, gelatin, and derivatives thereof. In other embodiments, the crystallization inhibitor may be selected from the group consisting of polyvinylpyrrolidone (PVP) and its derivatives such as PVP K12, hydroxypropylcellulose (HPC), hydroxyethylcellulose (HEC), hydroxypropyl methylcellulose (HPMC), polyvinylpyrrolidone-vinyl acetate (PVP/VA) Copolymer, copolymers of methacrylic acid, polyvinylpyrrolidone (PVP) and its derivatives; dextrin derivatives; polyethylene glycol (PEG); polypropylene glycol (PPG), polyvinyl alcohol (PVA), and poloxamers. In one embodiment, the crystallization inhibitor is a poloxamer. In one embodiment, the crystallization inhibitor is HPC.

In some embodiments, the crystallization inhibitor comprises between about 1%-5%, 5% to about 10% by weight (wt %) of total weight of the composition.

In certain embodiments, the permeation enhancer is selected from the group consisting of aliphatic alcohols, fatty acids having chain of 4 to 8 or 8 to 20 carbons, fatty acid esters, alcohol amines, polyhydric alcohol alkyl ethers, polyoxyethylene alkyl ethers, glycerides, middle-chain fatty acid esters of polyhydric alcohols having chain of 4-8, 8-20 carbon atoms, alkyl esters having chain of 1-6 carbon atoms, acylated amino acids, pyrrolidone, pyrrolidone derivatives, and ethoxylated fatty alcohols. In some non-limiting embodiments, the permeation enhancer is selected from the group consisting of medium chain triglycerides, diethylene glycol monoethyl ether, laurylglycol, oleoyl polyoxyl-6 glycerides, propylene glycol monocaprylate and caprylocaproyl polyoxyl-8 glycerides.

In certain embodiments, the solubilizer is selected from the group consisting of polysorbate, span, surfactants, propylene glycol monocaprylate and its derivatives, glycols and its derivatives, triglycerides and its derivatives, diethylene glycol monoethyl ether, cyclodextrins, polyhydric alcohol, polyethylene glycol, tetrahydrofurfuryl alcohol, diethyl tolumide, monoisopropylidene glycerine, sulfoxides, and similar chemicals such as but not limited to dimethylsulfoxide, dimethylacetamide, dimethylformamide, decylmethylsulfoxide, dimethylisosorbide, caprylocaproyl polyoxyl-8 glycerides, triacetine, and combinations thereof.

In certain embodiments, the adhesive component comprises first adhesive, the first adhesive comprising a polymer based on acrylic acid and its esters, isobutylenes, ethylene-vinyl acetate copolymers, natural rubbers, synthetic rubbers, styrene-diene copolymers, styrene-butadiene block copolymers, isoprene block copolymers, acrylonitrile-butadiene rubber, butyl rubber and neoprene rubber, pressure sensitive adhesives based on silicone, hot-melt adhesive, mixtures of esters of hydrogenated colophony with cellulose derivatives, and combinations thereof. In some non-limiting embodiments, the adhesive component comprises an acrylic-based polymer such as poly(acrylic acid) with viscosity average molecular weight ranges of about 100,000 to about 200,000, about 200,000 to about 400,000, about 400,000 to about 600,000, about 600,000 to about 800,000, about 800,000 to about 1,000,000, about 1,000,000 to about 2,000,000, about 2,000,000 to about 3,000,000, about 3,000,000 to about 4,000,000. In certain embodiments, the acrylic-based polymer may be selected from the group consisting of Duro-Tak™ 87-235A (DT 235A), Duro-Tak™ 87-4098 (D 4098), Duro-Tak™ 87-2510 (DT2510), Duro-Tak™ 87-9301 (DT9301), Duro-Tak™ 87-900A (DT900A), Duro-Tak™ 87-9088 (DT9088), and combinations thereof.

The present disclosure also provides a transdermal drug delivery system comprising an oil-in-water microemulsion comprising clobazam or a pharmaceutically acceptable salt thereof, at least one excipient, an oily phase, a hydrophilic phase and a solvent/co-solvent. In some embodiments, the excipient may be selected from the group consisting of medium chain triglycerides, Span, diethylene glycol monoethyl ether, propylene glycol monolaurate, oleoyl polyoxyl-6 glycerides, propylene glycol monocaprylate, caprylocaproyl polyoxyl-8 glycerides, Tween-20, Kolliphor derivates, and any combination thereof. In other embodiments, the oily phase may be selected from the group consisting of 4-allyl-2-ethoxyphenol, levulinic acid, lactic Acid, peg-6 caprylic/capric glycerides, sodium lauryl sulfoacetate (and) disodium laureth sulfosuccinate, pyruvic acid, and any combination thereof. In other embodiments, the hydrophilic phase may be selected from the group consisting of benzyl alcohol, polyethylene glycol, ethyl levulinate, phenoxy ethanol, phenyl acetate, and/or triacetine. In other embodiments, the solvent/co-solvent may be selected from the group consisting of DMSO, DMI, acrylic acid, NMP and any combination thereof.

In some embodiments, the microemulsion comprises clobazam or a pharmaceutically acceptable salt thereof in an amount from about 1% to about 15% by weight (wt %) relative to total weight of the microemulsion. In other embodiments, the microemulsion comprises clobazam or a pharmaceutically acceptable salt thereof in an amount from about 5% to about 10% by weight (wt %) relative to total weight of the microemulsion.

In some embodiments, the clobazam or a pharmaceutically acceptable salt thereof is in an amount ranging from about 5% to 15% by weight (wt %) relative to total weight of the drug-containing layer. In one embodiment, the clobazam or a pharmaceutically acceptable salt thereof is in an amount ranging from about 5% to about 20%, about 20% to about 40%, about 40% to 60%, about 60 to about 80% by weight (wt %) relative to total weight of the drug-containing layer.

In some embodiments, wherein the hydrophilic phase comprises between about 25% to about 50% by weight (wt %) of the total weight of microemulsion.

In some embodiments, the oily phase comprises between about 1% to about 20% by weight (wt %) of the total weight of microemulsion.

In some embodiments, the solvent comprises between about 15% to about 30% by weight (wt %) of the total weight of microemulsion.

In some embodiments, the surfactant/penetration enhancer comprises between about 10% to about 40% by weight (wt %) of the total weight of microemulsion.

In some embodiments, the microemulsion comprises between about 50% to about 80% by weight (wt %) of the total weight of the composition.

In some embodiments, the drug-containing layer further comprises an antioxidant.

In some embodiment, the transdermal delivery system further comprises an intermediate adhesive layer comprising a second adhesive and optionally an enhancer, wherein the clobazam or a pharmaceutically acceptable salt thereof has a lower solubility in the intermediate adhesive layer than the drug-containing layer. In some embodiments, the intermediate adhesive layer is located between the drug-containing layer and the impermeable backing layer. In some embodiments, the second adhesive in the intermediate adhesive layer is the same as the adhesive in the drug-containing layer. In some embodiments, the second adhesive in the intermediate adhesive layer is different from the adhesive in the drug-containing layer.

In one embodiment, the composition is stable in room temperature for one to 4 months with impurities less than 5%.

In certain embodiments, the drug-containing layer of the present transdermal drug delivery system (or the present composition) comprises clobazam (free base). In certain embodiments, the drug-containing layer of the present transdermal drug delivery system (or the present composition) comprises a pharmaceutically acceptable salt of clobazam.

In one embodiment, the transdermal drug delivery system provides a flux rate of more than about 0.5 $\mu g/cm^2 \cdot hr$ and less than about 30 $\mu g/cm^2 \cdot hr$ for about 24-36 hours, about 36-48 hours, about 48-60 hours, about 60-72 hours, about 72-84 hours, about 84-96 hours, about 96-108 hours, about 108-120 hours, about 120-132 hours, about 132-144 hours, about 144-156 hours, or about 156-168 hours.

Provided in the present disclosure is a method for treating a neurological disorder comprising the step of applying the disclosed transdermal patch to a human subject in need thereof.

In certain embodiments, the neurological disorders comprise epilepsy, seizure, LGS, anxiety or related disorders.

In one embodiment, the transdermal drug delivery system is applied to the human subject for a period of about 24 hours.

In certain embodiments, about 1 mg to about 3 mg, about 3 mg to about 5 mg, about 5 to about 10 mg, about 10 mg to 12 mg, about 12 mg to about 15 mg, about 15 mg to about 20 mg of clobazam is delivered from the transdermal drug delivery system to the human subject daily.

In one embodiment, about 3 mg to about 12 mg of clobazam is delivered from the transdermal drug delivery system to the human subject daily.

In one embodiment, about 1-20 mg, 20-30 mg, 30-40 mg, 40-50 mg, 50-60 mg, 60-70 mg, 70-80 mg, 80-90 mg/day is delivered from the transdermal drug delivery system to the human subject daily.

In some embodiments, the subject achieves 2000 ng/ml plasma concentration of clobazam about 2-24 hours after administration of the patch.

The present disclosure further provides a method of preparing a transdermal drug delivery system for administration of clobazam or a pharmaceutically acceptable salt thereof, the method comprising the step of: (a) preparing an oily phase by mixing clobazam or a pharmaceutically acceptable salt thereof, an oily component and a solvent; (b) preparing a hydrophilic phase comprising a surfactant; (c) adding to the oily phase and/or the hydrophilic phase one or more excipients selected from the group consisting of a permeation enhancer, a solubilizer and combinations thereof; (d) mixing the oily phase with the hydrophilic phase to obtain an oil-in-water microemulsion; (e) adding an adhesive and optionally a polymer to the microemulsion to obtain an adhesive composition; (f) providing an impermeable backing layer; and (g) applying the adhesive composition to the backing layer so as to obtain a transdermal drug delivery system.

4.1 BRIEF DESCRIPTION OF THE DRAWINGS

Figure 3:
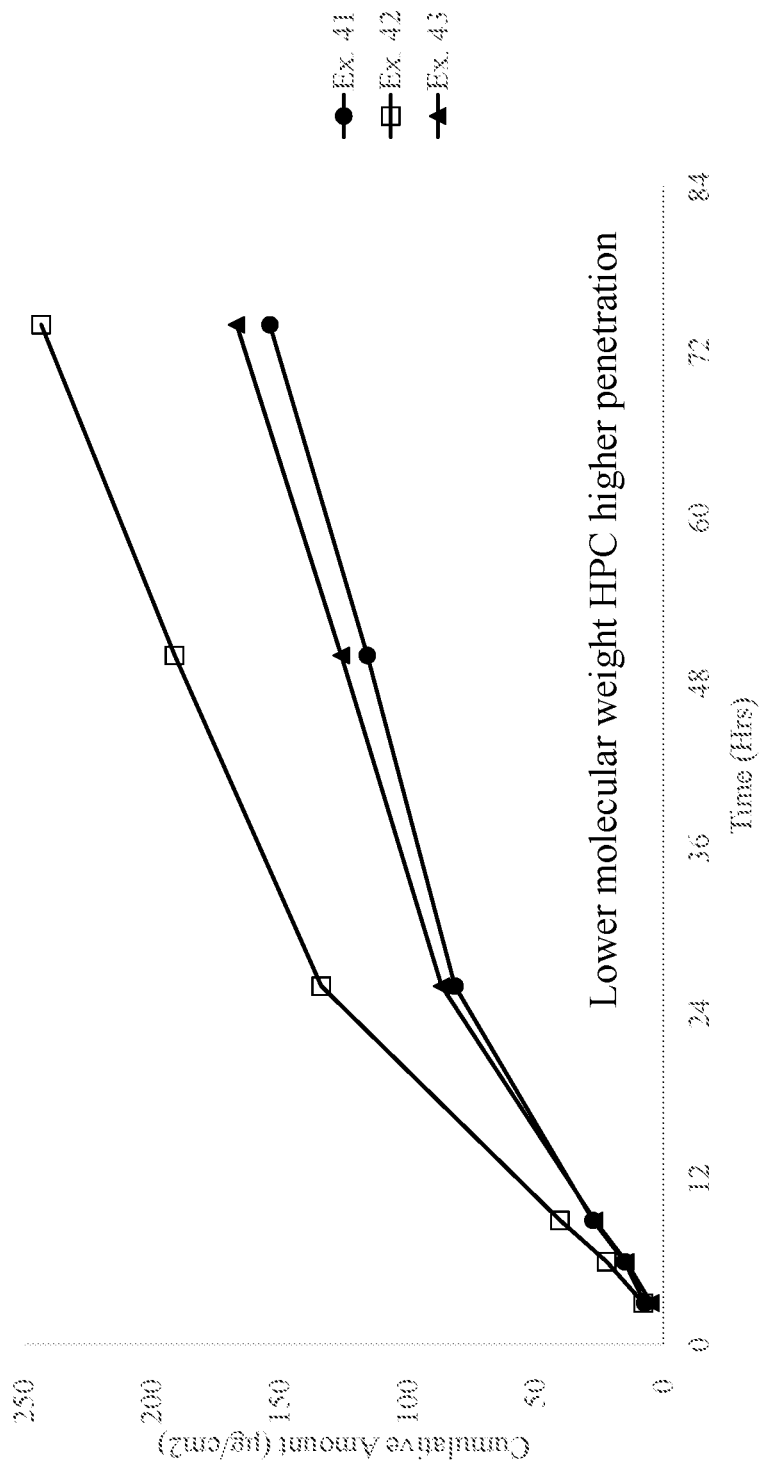

FIG. 3 shows clobazam release from the transdermal delivery (TDD) matrix system through human cadaver skin as a function of polymer molecular weight. ●=Example 41 (-); □=Example 42 ($HPC_L$); ▲=Example 43 ($Klucel_{HF}$). $Klucel_{HF\ 1}$, 150,000 (molecular weight Daltons), $HPC_L$ 140,000 (molecular weight Daltons), $HPC_{EF}$ 80,000 (molecular weight Daltons), and $HPC_{SSL}$ 40,000 (molecular weight Daltons).

Figure 4:
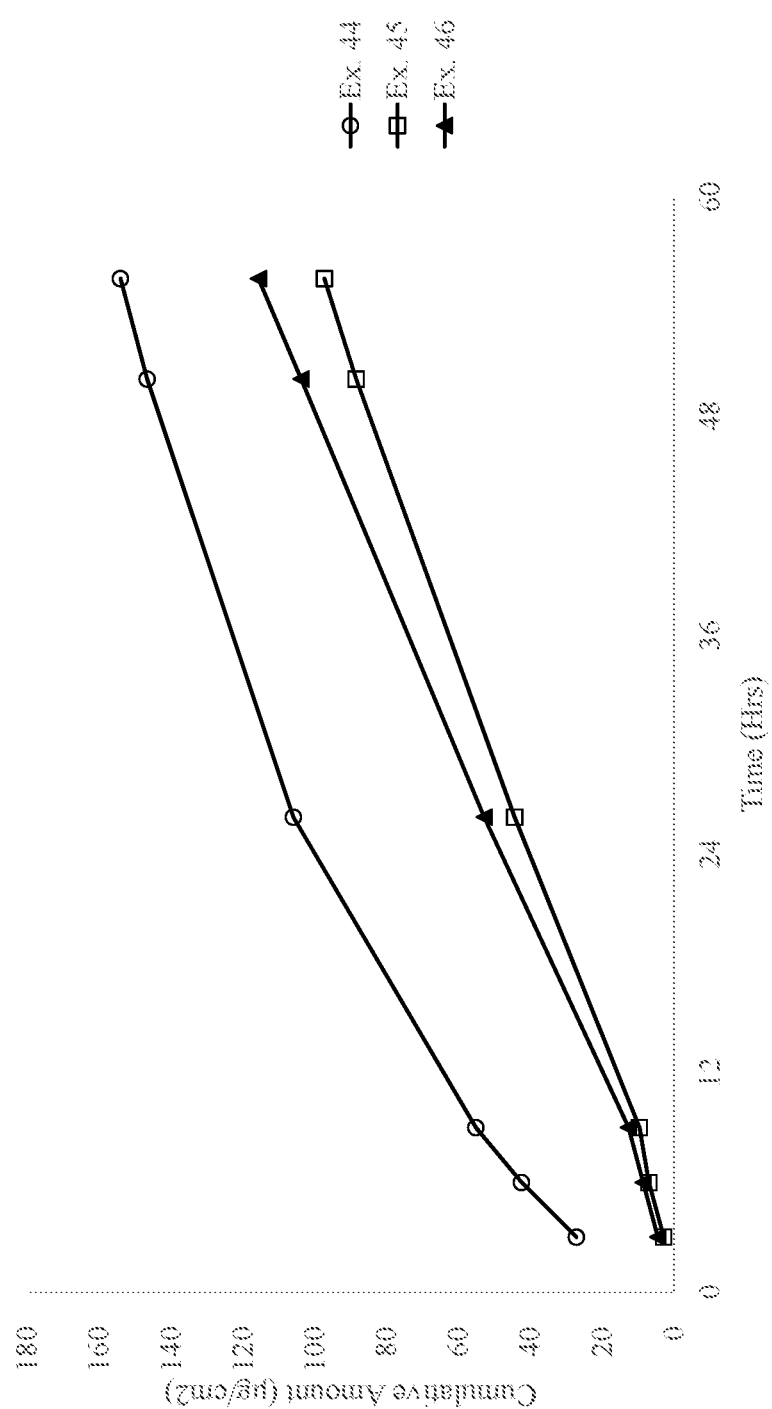
Figure 5A:
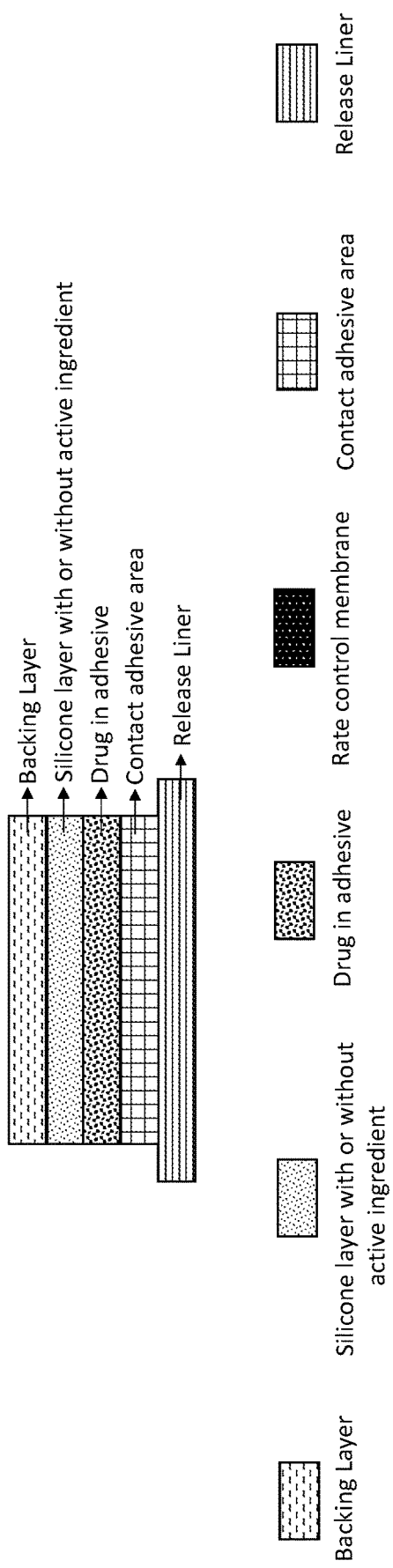
Figure 5B:
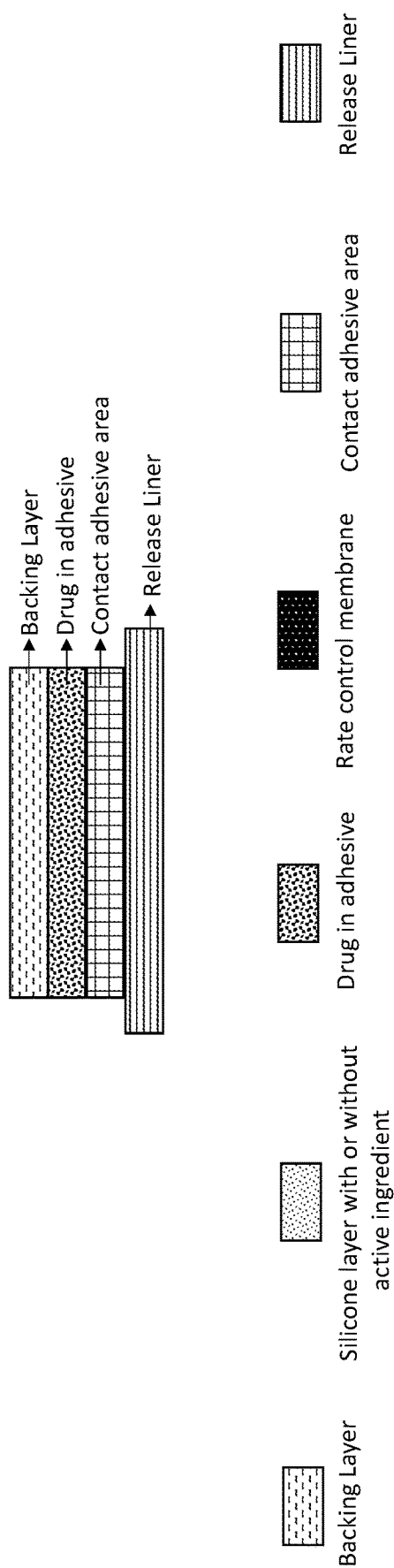
Figure 5C:
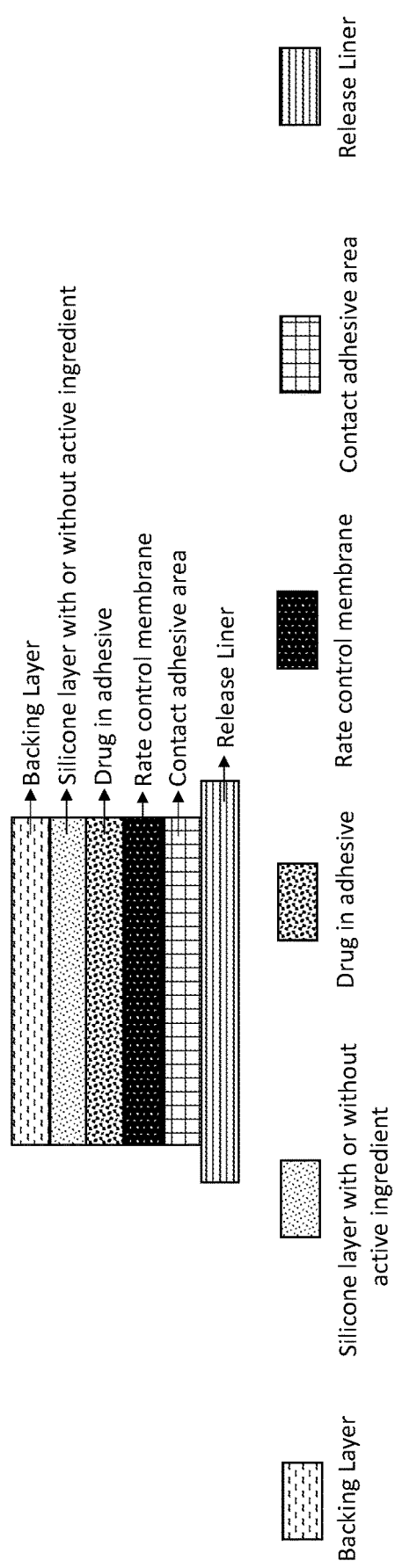
Figure 5D:
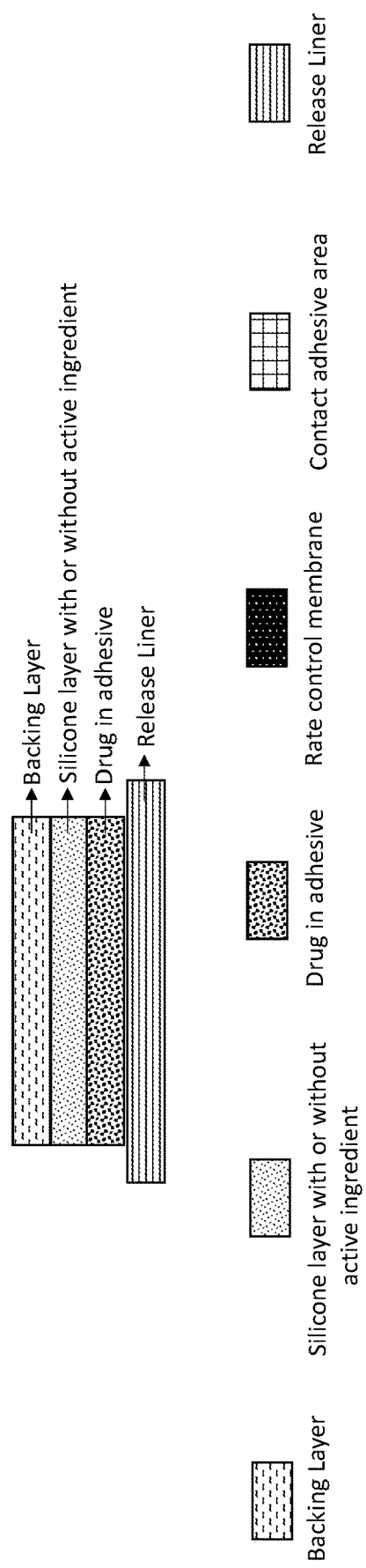
Figure 5E:
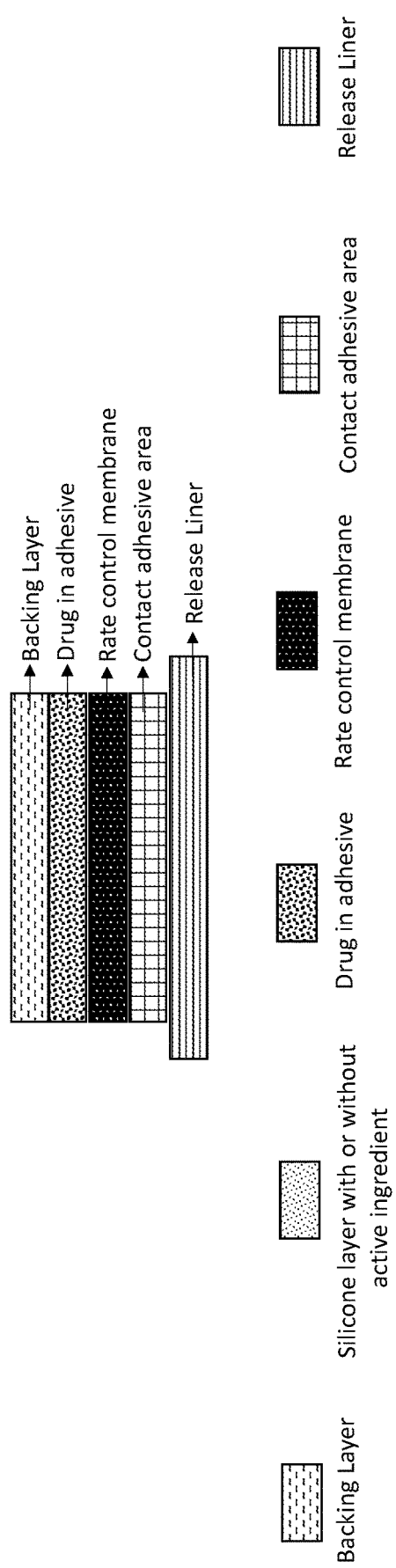
Figure 5F:
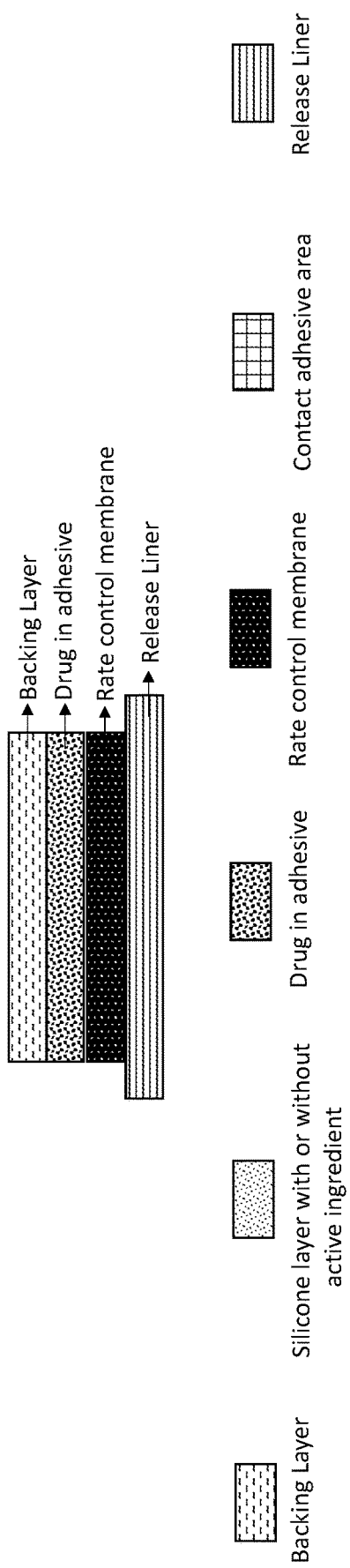

FIG. 4 shows clobazam release from the transdermal delivery (TDD) matrix system through human cadaver skin as a function of HPC molecular weight. ○=Example 44 ($HPC_L$); □=Example 45 ($HPC_{EF}$); ▲=Example 46 ($HPC_{SSL}$).

FIGS. 5A-5F show certain embodiments of the delivery device.

Figure 6:
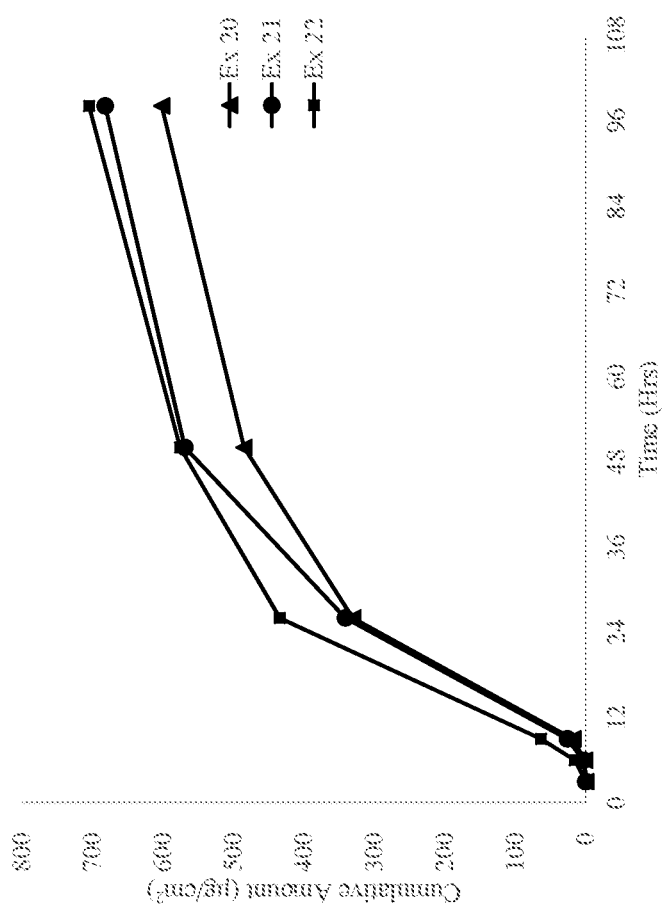

FIG. 6 shows the graph of penetration study for Examples 20, 21 and 22.

Figure 7:
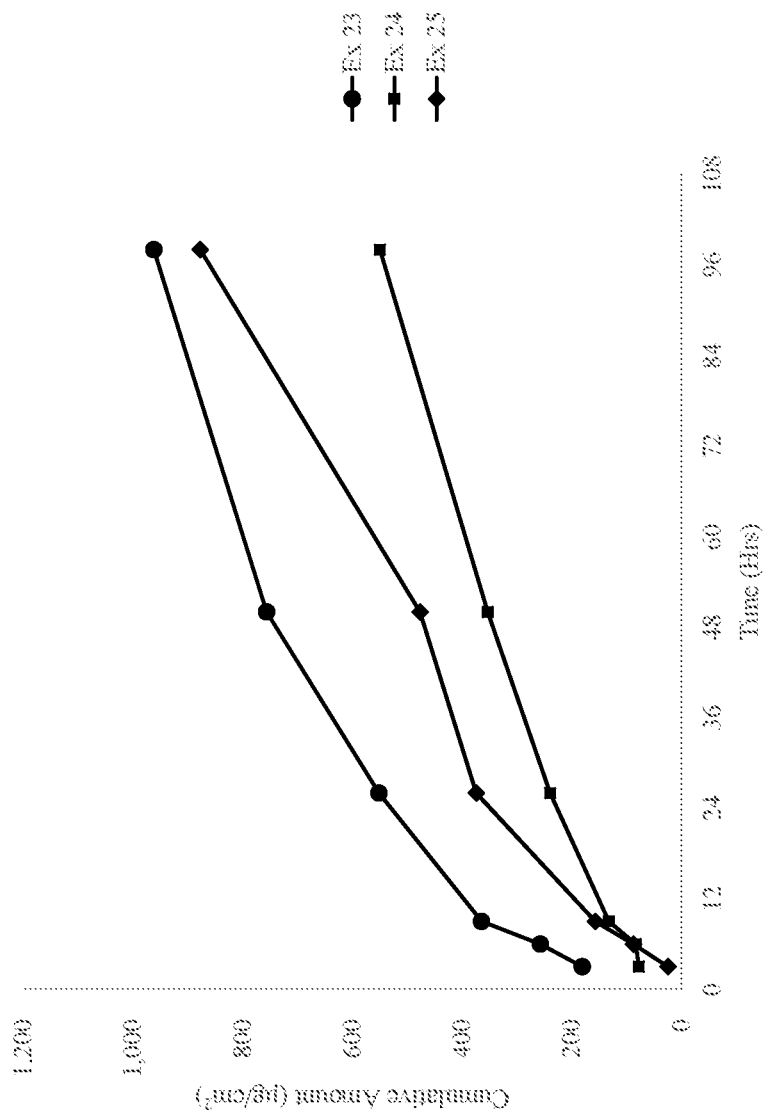

FIG. 7 shows the graph of penetration study for Examples 23, 24, and 25.

Figure 8:
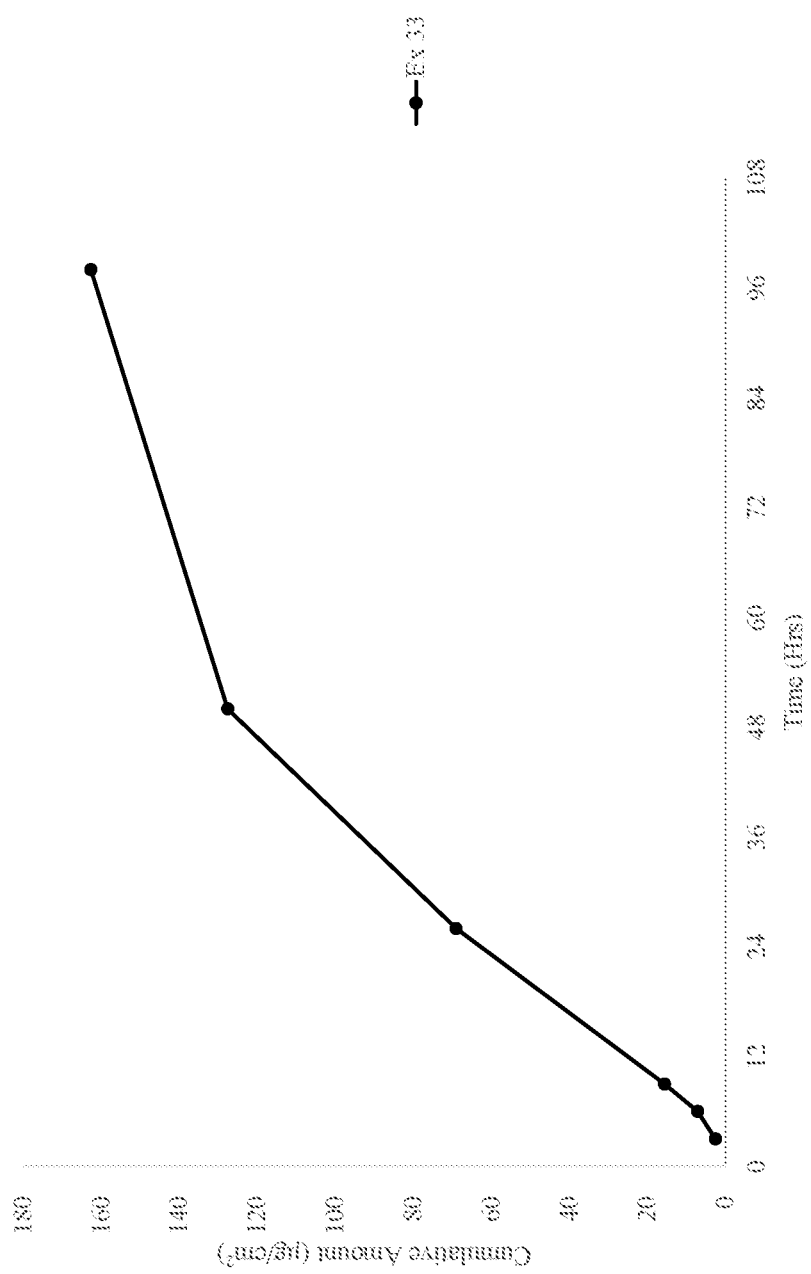

FIG. 8 shows the graph of penetration study for Example 33.

Figure 9:
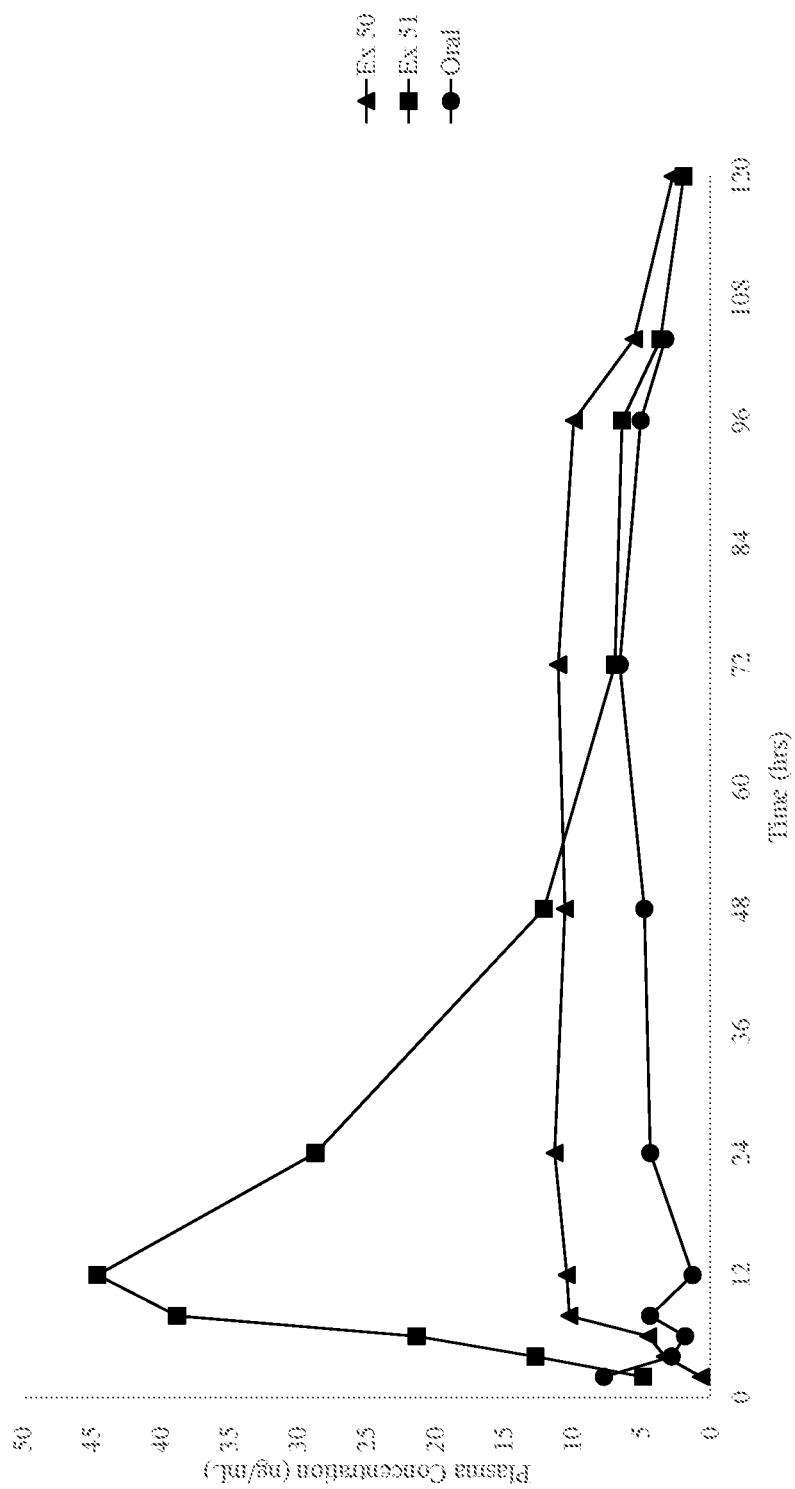

FIG. 9 shows the graph of plasma level of Clobazam from minipig over time for Examples 50 and 51.

4.2 DEFINITIONS

As used herein, the singular forms "a", "an" and "the" include plural referents unless the context clearly indicates otherwise. Thus, for example, reference to "an ingredient" includes mixtures of ingredients, reference to "an active pharmaceutical agent" includes more than one active pharmaceutical agent, and the like.

The terms "active agent", "pharmacologically active agent" and "drug" are used interchangeably herein to refer to a chemical material or compound that includes a desired pharmacological, physiological effect and include agents that are therapeutically effective. The terms also encompass pharmaceutically acceptable, pharmacologically active derivatives and analogs of those active agents specifically mentioned herein, including, but not limited to, salts, esters, amides, prodrugs, active metabolites, inclusion complexes, enantiomers S(−) or R(+), analogs of the active agent (e.g., clobazam).

The compounds of the present disclosure may be a salt. As used herein, a "salt" is a salt of the present compound which has been modified by making acid or base, salts of the compounds. The salt may be pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The present methods also encompass administering a physiologically functional derivative of the present compound. As used herein, the term "physiologically functional derivative" refers to a compound (e.g., a drug precursor) that is transformed in vivo to yield the present compound or its active metabolite, or a pharmaceutically acceptable salt, hydrate or solvate of the compound. The transformation may occur by various mechanisms (e.g., by metabolic or chemical processes), such as, for example, through hydrolysis.

Prodrugs are such derivatives, and a discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

As used herein, the term "about" as a modifier to a quantity is intended to mean + or −10% inclusive of the quantity being modified.

As used herein, "wt %", "% w/w" or "% (w/w)" refer to % by weight of the composition.

As used herein, "transdermal drug delivery system" refers to a system (e.g., a device) comprising a composition that releases drug upon application to the skin (or any other surface noted above). A transdermal drug delivery system may comprise a drug-containing composition, and, optionally, a backing layer and/or a release liner layer. In some embodiments, the transdermal drug delivery system is a substantially non-aqueous, solid form, capable of conforming to the surface with which it comes into contact, and capable of maintaining such contact so as to facilitate topical application without adverse physiological response, and without being appreciably decomposed by aqueous contact during topical application to a subject. Many such systems are known in the art and commercially available, such as transdermal drug delivery patches. Typically, transdermal drug delivery systems are classified into one of two categories: matrix-type systems and reservoir-type systems.

The term "transdermal patch", or "dermal patch", as used herein is intended to refer to a self-contained, discrete dosage form that, when applied to skin, is designed to deliver the drug(s) through the skin into systemic circulation. Some characteristics of a transdermal patch include flux rate, lag time and stability. Flux rate relates to the rate at which the transdermal patch delivers clobazam. Lag time relates to the time required for clobazam blood concentration to reach steady state after application of the transdermal patch. Lag time preferably matches clobazam metabolic rate in order to minimize fluctuations in blood concentration between applications of successive transdermal patches. Lastly, stability relates to the amount of impurities that develops within the transdermal patch while in storage.

The present agent/composition may be administered therapeutically to achieve a therapeutic benefit ("treating") or prophylactically to achieve a prophylactic benefit ("preventing"). By therapeutic benefit is meant eradication or amelioration of the disorder or condition being treated, and/or eradication or amelioration of one or more of the symptoms associated with the disorder or condition. By prophylactic benefit is meant prevention or delay of the onset of the condition, and/or prevention or delay of the onset of one or more of the symptoms associated with the condition. In certain embodiments, an effective amount of the present agent/composition to be administered prevents the condition from developing or being exacerbated into more serious conditions.

"Treating" or "treatment" of a state, disorder or condition includes: (1) preventing or delaying the appearance of clinical symptoms of the state, disorder, or condition developing in a person who may be afflicted with or predisposed to the state, disorder or condition but does not yet experience or display clinical symptoms of the state, disorder or condition; or (2) inhibiting the state, disorder or condition, i.e., arresting, reducing or delaying the development of the disease or a relapse thereof (in case of maintenance treatment) or at least one clinical symptom, sign, or test, thereof; or (3) relieving the disease, i.e., causing regression of the state, disorder or condition or at least one of its clinical or sub-clinical symptoms or signs. The benefit to a subject to be treated is either statistically significant or at least perceptible to the patient or to the physician.

An effective amount of an agent/drug refers to a therapeutically effective amount or a prophylactically effective amount. A "prophylactically effective amount" refers to an amount effective, at dosages and for periods of time necessary, to achieve the desired prophylactic result. In certain embodiments, since a prophylactic dose is used in subjects prior to or at an earlier stage of a disorder, the prophylactically effective amount is less than the therapeutically effective amount. In certain embodiments, the prophylactically effective amount is similar to, identical to, or more than, the therapeutically effective amount. A therapeutically effective amount of a drug is an amount effective to demonstrate a desired activity of the drug. A therapeutically effective amount may vary depending on the compound, the disorder and its severity and the age, weight, physical condition and responsiveness of the subject to be treated. In certain embodiments, the drug-containing layer or the present composition further comprises a pharmaceutically acceptable carrier, vehicle, excipient and/or diluent.

5. DETAILED DESCRIPTION

The present disclosure provides a transdermal delivery system containing clobazam, or a pharmaceutically acceptable salt, derivative, or solvate thereof, as an active agent. In certain embodiments, the transdermal delivery system is a transdermal patch, adapted is for daily administration with minimal clobazam blood concentration fluctuations. In certain embodiments, the transdermal delivery system provides high flux of clobazam and low crystallization of the active agent.

The present disclosure also provides a topical composition containing clobazam, or a pharmaceutically acceptable salt, derivative, or solvate thereof, as an active agent.

The present disclosure provides a transdermal delivery system comprising: a drug-containing layer, and a backing layer.

Provided herein is a transdermal drug delivery system comprising: (a) a drug-containing layer comprising: (i) an oil-in-water microemulsion comprising: an oily phase comprising clobazam or a pharmaceutically acceptable salt thereof, a solvent and an oily component; and a hydrophilic phase comprising a surfactant, the microemulsion further comprising a permeation enhancer and/or solubilizer; and (ii) an adhesive component; and (b) an impermeable backing layer. In some embodiments, the transdermal drug delivery system is in the form of a transdermal pressure sensitive patch.

Provided herein is a transdermal drug delivery system comprising: (a) a drug-containing layer comprising (i) an oil-in-water microemulsion comprising: an oily phase comprising clobazam or a pharmaceutically acceptable salt thereof, a solvent and an oily component; and a hydrophilic phase comprising a surfactant, the microemulsion further comprising a permeation enhancer and/or solubilizer; and (ii) an adhesive component comprising a first adhesive, wherein the adhesive component comprises between about 30% and less than about 50% of the drug-containing layer; and (b) an impermeable backing layer. In some embodiments, the transdermal drug delivery system is in the form of a transdermal patch.

Provided herein is a transdermal drug delivery system comprising: (a) a drug-containing layer comprising (i) an oil-in-water microemulsion comprising: an oily phase comprising clobazam or a pharmaceutically acceptable salt thereof, an oily component and a solvent; and a hydrophilic phase comprising a surfactant, the microemulsion further comprising at least one of a permeation enhancer and/or a solubilizer; and (ii) an adhesive component comprising a first adhesive, wherein the adhesive component comprises about 10-15%, 15-20%, 20-25%, 25-30%, 30-35%, 35-40%, 40-45%, 45-50% and less than about 50% of the drug-containing layer; (b) an impermeable backing layer; (c) an intermediate backing layer comprising a second adhesive, wherein the clobazam or a pharmaceutically acceptable salt thereof has a lower solubility in the intermediate adhesive layer than the drug-containing layer; (d) optionally, a releasing membrane layer; (d) optionally, a contact adhesive layer; and (e) optionally, a release liner layer.

In some embodiments, the drug-containing layer is in the form of a polymer matrix combined with a pressure sensitive adhesive system. In other embodiments, the drug-containing layer is in the form of a microemulsion combined with a pressure-sensitive adhesive system. In other embodiments, the drug-containing layer is in the form of a drug with enhancer layer combined with a pressure sensitive adhesive system.

In some embodiments, the transdermal delivery system is a micro-reservoir system comprising a polymer matrix system combined with pressure sensitive adhesive system. In some embodiments, the transdermal delivery system is a micro-reservoir system comprising microemulsion with pressure sensitive adhesive system.

5.1 Clobazam

The active ingredient in the transdermal delivery systems of the present disclosure is clobazam or a pharmaceutically acceptable salt thereof.

Clobazam is practically insoluble in water at 25° C., with solubility of 70 microgram/ml (μg/ml). Clobazam is chemically designated 1-phenyl-5-methyl-8-chloro-1,2,4,5-tetrahydro-2,4-dioxo-3H-1,5-benzodiazepine 7-Chloro-1-methyl-5-phenyl-1,5-dihydro benzo[b][1,4]diazepine-2,4-dione, and is represented by the following chemical structure:

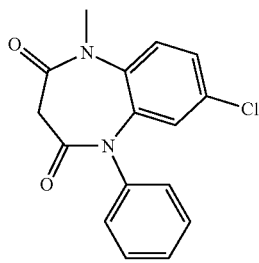 [SMILES: CN1C(=O)CC(=O)N(c2ccccc2)c2cc(Cl)ccc21]

In certain embodiments, the transdermal delivery systems of the present disclosure comprise clobazam in the free base form. In certain embodiments, the transdermal delivery systems of the present invention comprise a pharmaceutically acceptable salt of clobazam. In certain embodiments, the salt of clobazam is an acid addition salt formed by treatment with an appropriate acid, such as a hydrohalic acid, for example hydrochloric or hydrobromic acid, sulfuric acid, nitric acid, phosphoric acid, acetic acid, propanoic acid, hydroxyacetic acid, 2-hydroxypropanoic acid, 2-oxopropanoic acid, ethanedioic acid, propanedioic acid, butanedioic acid, (Z)-2-butenedioic acid, (E)-2-butenedioic acid, 2-hydroxybutanedioic acid, 2,3-dihydroxybutanedioic acid, 2-hydroxy-1,2,3-propanetricarboxylic acid, methanesulfonic acid, ethanesulfonic acid, benzenesulfonic acid, 4-methylbenzenesulfonic acid, cyclohexanesulfamic acid, 2-hydroxybenzoic acid or 4-amino-2-hydroxybenzoic acid. In one embodiment, the present transdermal delivery system comprises the HCl salt of clobazam.

In certain embodiments, the transdermal delivery systems of the present disclosure comprise an ester of clobazam.

In certain embodiments, clobazam or its pharmaceutically acceptable salt thereof is in an amount ranging from about 0.1% to about 0.5% by weight (wt %), from about 0.5% to about 1% by weight (wt %), from about 1% to about 2% by weight (wt %), from about 2% to about 3% by weight (wt %), from about 3% to about 4% by weight (wt %), from about 4% to about 5% by weight (wt %), from about 5% to about 6% by weight (wt %), from about 6% to about 7% by weight (wt %), from about 7% to about 8% by weight (wt %), from about 8% to about 9% by weight (wt %), from about 9% to about 10% by weight (wt %), from about 10% to about 11% by weight (wt %), from about 11% to about 12% by weight (wt %), from about 12% to about 13% by weight (wt %), about 13% to about 14% by weight (wt %), about 14% to 15% by weight (wt %), about 15% to about 16% by weight (wt %), about 16% to 17% by weight (wt %), about 17% to 18% by weight (wt %), or about 18% to 19% by weight (wt %), or about 19% to 20% by weight (wt %), relative to the total weight of the drug-containing layer (or the total weight of the composition).

The clobazam or salt thereof may be present in the pharmaceutical composition in combination with another active pharmaceutical ingredient. Suitable active pharmaceutical ingredients for combination with clobazam would be known to those of skill in the art, as further described herein below.

In certain embodiments, clobazam is prepared or obtained, and further purified. In certain embodiments, clobazam may be purified by dissolving the clobazam in a chlorinated solvent, such as methylene chloride, ethylene chloride, chloroform, preferably methylene chloride, and heating the reaction mixture. The chlorinated solvent may be mixed with a second solvent, such as methanol. The solution of clobazam may then be concentrated by heating, distilling and the then cooling the reaction mixture. The pure clobazam is then isolated using a suitable solvent, such as acetone, methanol, ethyl acetate, isopropyl alcohol, methyl isobutyl ketone (MIBK), acetonitrile, isopropyl acetate, toluene, preferably methanol. The isolation step comprises filtering the product, washing the product in the suitable solvent, and then drying under vacuum.

5.2 Microemulsion

In some embodiments, the present disclosure provides a transdermal drug delivery system comprising a drug-containing layer comprising (i) an oil-in-water microemulsion comprising: an oily phase comprising clobazam or a pharmaceutically acceptable salt thereof, an oily component and a solvent; and a hydrophilic phase comprising a surfactant. The microemulsion further comprises at least one of a permeation enhancer and/or solubilizer. If present, and depending on their nature, the permeation enhancer and/or solubilizer may partition into the hydrophilic phase of the microemulsion, the oily phase of the microemulsion, or a combination thereof.

In some embodiments, the microemulsion is transparent or substantially transparent. In some embodiments, the microemulsion is optically transparent or substantially optically transparent. In some embodiments, the microemulsion is translucent or substantially translucent. In other embodiments, the microemulsion is opaque.

As defined herein, "transparent" (or translucent) is the physical property of allowing light to pass through the material without appreciable scattering of light.

Oily Phase

In certain embodiments, the oily phase comprises an oily component. In certain embodiments, the oily component is one or more oils selected from the group consisting of aromatic oils, mineral oils, plant oils, animal oils, synthetic oils, silicone oils, fluoro oils, and any combination thereof.

Exemplary oils that may be used in the present composition, include mineral oils (liquid petroleum jelly), plant oils (liquid fraction of karite butter, sunflower oil), animal oils (perhydrosqualene), synthetic oils (purcellin oil), silicone oils (cyclomethicone) and fluoro oils (perfluoropolyethers). Fatty alcohols and fatty acids (e.g., stearic acid) can be added to these oils.

In certain embodiments, the oily phase further comprises one or more excipients selected from the group consisting of alkyl benzoates, carboxylic acids, surfactants, emulsifiers, and any combination thereof. In some non-limiting embodiments, the oily phase comprises 4-allyl-2-ethoxyphenol (2-Methoxy-4-(prop-2-en-1-yl) phenol), levulinic acid, lactic acid, peg-6 caprylic/capric glycerides, pyruvic acid, and/or sodium lauryl sulfoacetate (and) disodium laureth sulfosuccinate.

In certain embodiments, the oil (or a combination of oils) is in an amount ranging from about 0.5% to about 1% by weight (wt %), from about 1% to about 2% by weight (wt %), from about 2% to about 5% by weight (wt %), from about 15% to about 20% by weight (wt %), from about 20% to about 25% by weight (wt %), from about 25% to about 30% by weight (wt %), from about 30% to about 35% by weight (wt %), from about 35% to about 40% by weight (wt %), from about 40% to about 45% by weight (wt %), from about 45% to about 50% by weight (wt %), from about 50% to about 55% by weight (wt %), or from about 55% to about 60% by weight (wt %), relative to the total weight of the drug-containing layer (or the total weight of the composition).

Solvent

Solvents are used in the oily phase to solubilize the clobazam active ingredient. Solvents that may be used in the microemulsions of the compositions include, but are not limited to, C1-C20 alcohols, polyhydric alcohols, isopropyl myristate, glycols selected from the group consisting of propylene glycol (PG), polyethylene glycol (PEG), dipropylene glycol and hexylene glycol; glycerine, imidazolidinones, 1,3-dimethyl-2-imidazolidinone (DMI), pyrrolidones selected from the group consisting of N-methyl 2-pyrrolidone (NMP), 2-pyrrolidone; sulfoxides selected from the group consisting of dimethyl sulfoxide and decyl methyl sulfoxide; dimethyl isosorbide, mineral oils, vegetable oils, and carboxylic acids selected from the group consisting of acrylic acid, lactic acid, pyruvic acid, and acetic acid.

In particular non-limiting embodiments, the solvent comprises dimethyl sulfoxide (DMSO), 1,3-dimethyl-2-imidazolidinone (DMI), acrylic acid, NMP, dichloromethane, chloroform, acetonitrile, acetone, ethyl acetate, methanol and toluene. In one example, the solvent is DMSO. In another example, the solvent is DMI Arlasolv. In another embodiment, the solvent is propylene glycol (PG).

Other of solvents that may be suitable for use in the microemulsions of the present disclosure include but are not limited to ethanol, isopropanol, butylene glycol, cremaphor EL, glycerol, isopropyl myristate, isopropyl palmitate, isopropyl stearate, diisopropyl adipate, labrafil, Caprylocaproyl polyoxyl-8 glycerides, oleic acid, mineral oil, myglyol, plurol oleic, propylene carbonate, propylene glycol, polyoxyethylene glycol (PEG), and silicone solvent like cyclomethicone, hexamethyldisiloxane, solutol, sorbitol, phenoxy ethanol, phenyl acetate, or transcutol.

In certain embodiments, the solvent (or a combination of solvents) is in an amount ranging from about 0.5% to about 1% by weight (wt %), from about 1% to about 2% by weight (wt %), from about 2% to about 5% by weight (wt %), from about 15% to about 20% by weight (wt %), from about 20% to about 25% by weight (wt %), from about 25% to about 30% by weight (wt %), from about 30% to about 35% by weight (wt %), from about 35% to about 40% by weight (wt %), from about 40% to about 45% by weight (wt %), from about 45% to about 50% by weight (wt %), from about 50% to about 55% by weight (wt %), or from about 55% to about 60% by weight (wt %), relative to the total weight of the drug-containing layer (or the total weight of the composition).

Hydrophilic Phase

In certain embodiments, the hydrophilic phase comprises a surfactant. The surfactants used in the present invention may be an anionic surfactant, a cationic surfactant, a zwitterionic surfactant, a nonionic surfactant, and mixtures thereof.

In some embodiments, the surfactant is an anionic surfactant, such as, but not limited to, alkyl benzene sulphonate, sodium dodecyl sulfate, sodium sulfosuccinate, sodium lauryl sulfate, an alkyl naphthalene sulfonate condensate sodium salt, sodium stearate, N-Lauryl Sarcosine, and sodium octyl sulfate, and mixtures thereof.

In other embodiments, the surfactant is a cationic surfactant such as, but not limited to, cetyl trimethyl ammonium bromide, cetyl trimethyl ammonium chloride, dodecyl pyridinium chloride, octyl trimethyl ammonium bromide, and mixtures thereof.

In other embodiments, the surfactant is a zwitterionic surfactants such as, but not limited to, hexadecyl trimethyl ammoniopropane sulfonate, oleyl betaine, lechitin, cocamidopropyl betaine and mixtures thereof.

In other embodiments, the surfactant is a nonionic surfactant such as, but not limited to, polyoxyethylene sorbitan fatty acids (polysorbate 20, 40, 60 and 80 (Tween)), sorbitan monolaurate, polyethylene glycol dodecyl ether, Triton X-100, ethoxylated sorbitan ester, a sorbitan ester, a polyglycerol ester, a sucrose ester, a poloxamer, an alkyl polyglucoside, a polyalkyleneoxide modified heptamethyltrisiloxane, an allyloxypolyethylene glycol methylether and mixtures thereof.

In certain embodiments, the surfactant may be selected from the group consisting of sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80), kolliphor derivats (macrogol ester), sodium lauryl sulfate, sorbitan esters selected form the group consisting of sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate and sorbitan tri-isostearate, lecithin, and pharmaceutical acceptable salts thereof and combinations thereof.

In certain embodiments, the surfactant (or a combination of surfactants) is in an amount ranging from about 0.5% to about 1% by weight (wt %), from about 1% to about 2% by weight (wt %), from about 2% to about 5% by weight (wt %), from about 15% to about 20% by weight (wt %), from about 20% to about 25% by weight (wt %), from about 25% to about 30% by weight (wt %), from about 30% to about 35% by weight (wt %), from about 35% to about 40% by weight (wt %), from about 40% to about 45% by weight (wt %), from about 45% to about 50% by weight (wt %), from about 50% to about 55% by weight (wt %), or from about 55% to about 60% by weight (wt %), relative to the total weight of the drug-containing layer (or the total weight of the composition).

Permeation Enhancers

Although no permeation enhancer (which includes absorption promoter) is needed in the present invention in that adequate clobazam flux can be achieved without permeation enhancer, if desired, permeation enhancer(s) can be used for further increasing the skin permeability of the drug clobazam or drug combinations to achieve delivery at therapeutically effective rates. Permeation enhancer(s) can be applied to the skin by pretreatment or currently with the drug. A permeation enhancer should have the ability to enhance the permeability of the skin for one, or more drugs or other biologically active agents. A useful permeation enhancer would enhance permeability of the desired drug or biologically active agent at a rate adequate for therapeutic level from a reasonably sized patch (e.g., about 20 to 80 $cm^2$).

In certain embodiments, the permeation enhancer is an alcohol, glycols, glycol esters, a fatty acid, a fatty alcohol, or combinations thereof.

In certain embodiments, the permeation enhancer may be selected from the group consisting of aliphatic alcohols, fatty acids having chain of 4 to 8 carbon atoms or 8 to 20 carbon atoms, fatty acid esters, alcohol amines, polyhydric alcohol alkyl ethers, polyoxyethylene alkyl ethers, glycerides, middle-chain fatty acid esters of polyhydric alcohols having chain of 4-8 carbon atoms or 8-20 carbon atoms, alkyl esters having chain of 1-6 carbon atoms, acylated amino acids, pyrrolidone, pyrrolidone derivatives, and ethoxylated fatty alcohols.

Other examples of permeation enhancers may include, but are not limited to, fatty acids (e.g. Oleic Acid, linoleic acid, linolenic acid); keto acids (e.g. pyruvic acid, acetoacetic acid); fatty esters (e.g. isopropyl myristate, sodium oleate, methyl laurate); azone/azone-like compounds (N-decyl-2-pyrrolidone, dodecyl amine, PP, nicotine sulfate); and others (e.g., menthol, methyl pyrrolidone, cineole, limonene).

Other examples of permeation enhancers may include, but re not limited to, aliphatic alcohols, including, but not limited to, saturated or unsaturated higher alcohols having 12 to 22 carbon atoms, such as oleyl alcohol and lauryl alcohol; saturated or unsaturated fatty acid having a chain of 4 to 8 carbon atoms, 8 to 20 carbon atoms, such as but not limited to linoleic acid, oleic acid, linolenic acid, stearic acid, isostearic acid and palmitic acid; fatty acid esters, such as but not limited to isopropyl myristate, diisopropyl adipate and isopropyl palmitate; alcohol amines, such as but not limited to triethanolamine, triethanolamine hydrochloride and diisopropanolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g. —$OCH_2CH_2$—) of the polyoxyethylene chain is 1 to 9, such as but not limited to diethylene glycol monoethyl ether, polyoxyethylene lauryl ether, polyoxyethylene cetyl ether, polyoxyethylene stearyl ether and polyoxyethylene oleyl ether; glycerides (i.e., fatty acid esters of glycerol), such as but not limited to glycerol esters of fatty acids having 6 to 18 carbon atoms, where the glycerides may be monoglycerides (i.e., a glycerol molecule covalently bonded to one fatty acid chain through an ester linkage), diglycerides (i.e., a glycerol molecule covalently bonded to two fatty acid chains through ester linkages), triglycerides (i.e., a glycerol molecule covalently bonded to three fatty acid chains through ester linkages), or combinations thereof, where the fatty acid components forming the glycerides include, but are not limited to octanoic acid, decanoic acid, dodecanoic acid, tetradecanoic acid, hexadecanoic acid, octadecanoic acid (i.e., stearic acid) and oleic acid; middle-chain fatty acid esters of polyhydric alcohols with aliphatic tails of 6-20 carbon atoms; alkyl esters such as but not limited to lactic acid alkyl esters and dibasic acid alkyl esters with chain of 1 to 6 carbon atoms; acylated amino acids; pyrrolidone; pyrrolidone derivatives; and combinations thereof.

In some non-limiting embodiments, the permeation enhancer may comprise one or more of benzyl alcohol, polyethylene glycol, ethyl levulinate, phenoxy ethanol, phenyl acetate, and/or triacetin.

In other non-limiting embodiments, the permeation enhancer is selected from the group consisting of medium chain triglycerides, diethylene glycol monoethyl ether, propylene glycol monolaurate, oleoyl polyoxyl-6 glycerides, propylene glycol monocaprylate and caprylocaproyl polyoxyl-8 glycerides.

In certain embodiments, the permeation enhancer is 1,2-propyleneglycol, a polysorbate (e.g., polysorbate 80 or Tween 80), kolliphor derivates, hydroxypropyl cellulose (HPC), or combinations thereof.

In certain embodiments, the permeation enhancer (or a combination of permeation enhancers) is in an amount ranging from about 0.5% to about 1% by weight (wt %), from about 1% to about 2% by weight (wt %), from about 2% to about 5% by weight (wt %), from about 15% to about 20% by weight (wt %), from about 20% to about 25% by weight (wt %), from about 25% to about 30% by weight (wt %), from about 30% to about 35% by weight (wt %), from about 35% to about 40% by weight (wt %), from about 40% to about 45% by weight (wt %), from about 45% to about 50% by weight (wt %), from about 50% to about 55% by weight (wt %), or from about 55% to about 60% by weight (wt %), relative to the total weight of the drug-containing layer (or the total weight of the composition). In some embodiments, the drug-containing layer of the transdermal delivery system (or the present composition) comprises two or more permeation enhancers in a total amount of about 10% of the drug-containing layer of the present dermal patch (or the present composition). In some embodiments, the present transdermal delivery system comprises two or more permeation enhancers in a total amount of about 15% of the drug-containing layer of the present transdermal delivery system (or the present composition). In some embodiments, the present transdermal delivery system comprises two or more permeation enhancers in a total amount of about 20% of the drug-containing layer of the present dermal patch (or the present composition).

Solubilizers

Solubilizers may be any one or more of the solvents described above, including but not limited to C1-C20 alcohols, polyhydric alcohols, isopropyl myristate, glycols selected from the group consisting of propylene glycol (PG), polyethylene glycol (PEG), dipropylene glycol and hexylene glycol; glycerine, imidazolidinones, 1,3-dimethyl-2-imidazolidinone (DMI), pyrrolidones selected from the group consisting of N-methyl 2-pyrrolidone (NMP), 2-pyrrolidone; sulfoxides selected from the group consisting of dimethyl sulfoxide and decyl methyl sulfoxide; dimethyl isosorbide, mineral oils, vegetable oils, and carboxylic acids selected from the group consisting of acrylic acid, lactic acid and acetic acid.

In certain embodiments, the solubilizer comprises dimethyl sulfoxide (DMSO), 1,3-dimethyl-2-imidazolidinone (DMI), acrylic acid, keto acids, NMP, dichloromethane, chloroform, acetonitrile, acetone, ethyl acetate, methanol and toluene. In one example, the solvent is DMSO. In another example, the solvent is DMI Arlasolv. In another embodiment, the solvent is propylene glycol (PG).

In certain embodiments, the solubilizer may be selected from the group consisting of polysorbate, span, surfactants, propylene glycol monocaprylate and its derivatives, glycols and its derivatives, triglycerides and its derivatives, diethylene glycol monoethyl ether, cyclodextrins, polyhydric alcohol, polyethylene glycol, tetrahydrofurfuryl alcohol, diethyl tolumide, monoisopropylidene glycerine, sulfoxides, and similar chemicals such as but not limited to dimethylsulfoxide, dimethylacetamide, dimethylformamide, decylmethylsulfoxide, dimethylisosorbide, caprylocaproyl polyoxyl-8 glycerides, triacetine, and combinations thereof.

In certain embodiments, the solubilizer (or a combination of solubilizers) is in an amount ranging from about 0.5% to about 1% by weight (wt %), from about 1% to about 2% by weight (wt %), from about 2% to about 5% by weight (wt %), from about 15% to about 20% by weight (wt %), from about 20% to about 25% by weight (wt %), from about 25% to about 30% by weight (wt %), from about 30% to about 35% by weight (wt %), from about 35% to about 40% by weight (wt %), from about 40% to about 45% by weight (wt %), from about 45% to about 50% by weight (wt %), from about 50% to about 55% by weight (wt %), or from about 55% to about 60% by weight (wt %), relative to the total weight of the drug-containing layer (or the total weight of the composition).

Antioxidants

In certain embodiments, the drug-containing layer of the present transdermal delivery system (or the present composition) further comprises an antioxidant. For example, the pharmaceutically acceptable antioxidant may be selected from the group consisting of ascorbic acid, sodium ascorbate, sodium bisulfate, sodium metabisulfate and monothio glycerol. α-Tocopherol, Gamma-tocopherol, Delta-tocopherol, Vitamin E, Butylated hydroxytoluene (BHT), Butylated hydroxyanisole (BHA), Tertiary-butyl hydroquinone (TBHQ), Propyl gallate, Octyl gallate, Dodecyl gallate, Sodium erythorbate, Erythorbic Acid, 4-Hexylresorcinl, Calcium ascorbate, Fatty acid esters of ascorbic acid (ascorbyl palmitate), or a combination thereof.

5.3 Adhesive

In certain embodiments, the adhesive in the drug-containing layer is a polymer based on acrylic acid and its esters, isobutylenes, ethylene-vinyl acetate copolymers, natural rubbers, synthetic rubbers, styrene-diene copolymers, styrene-butadiene block copolymers, isoprene block copolymers, acrylonitrile-butadiene rubber, butyl rubber and neoprene rubber, pressure sensitive adhesives based on silicone, hot-melt adhesive, mixtures of esters of hydrogenated colophony with cellulose derivatives, and combinations thereof.

In some embodiments, the adhesive layer comprises at least about 10-15%, 15-20%, 20-25%, 25-30%, 35-40%, 45-50% by weight based on the weight of the formulation. In other embodiments the adhesive layer comprises at least about 50% by weight based on the weight of the formulation. In other embodiments, the adhesive layer comprises between about 10-15%, 15-20%, 20-25%, 25-30%, 30-35%, 35-40%, 40-49% by weight based on the weight of the formulation. In other embodiments, the adhesive layer comprises between about 10-15%, 15-20%, 20-25%, 25-30%, 30-35%, 35-40%, 40-45% by weight or 45-50% by weight based on the weight of the formulation. In other embodiments, the adhesive layer comprises between about 10-15%, 15-20%, 20-25%, 25-30%, 30-35%, 35-40% by weight or 40-45%, 45-50% by weight based on the weight of the formulation. In other embodiments, the adhesive layer comprises between about 10-15%, 15-20%, 20-25%, 25-30% by weight, or 30-35%, 35-40% by weight based on the weight of the formulation. In other embodiments, the adhesive layer comprises about 10-15, 15-20%, 20-25%, 25-30%, 30-35%, 35-40%, 40-45%, or 45-50% weight based on the weight of the formulation. In other embodiments, the adhesive layer comprises about 32% weight based on the weight of the formulation. In other embodiments, the adhesive layer comprises about 34% weight based on the weight of the formulation. In other embodiments, the adhesive layer comprises about 36% weight based on the weight of the formulation. In other embodiments, the adhesive layer comprises about 38% weight based on the weight of the formulation. In other embodiments, the adhesive layer comprises about 40% weight based on the weight of the formulation. In other embodiments, the adhesive layer comprises about 42% weight based on the weight of the formulation. In other embodiments, the adhesive layer comprises about 44% weight based on the weight of the formulation. In other embodiments, the adhesive layer comprises about 46% weight based on the weight of the formulation. In other embodiments, the adhesive layer comprises about 48% weight based on the weight of the formulation. In other embodiments, the adhesive layer comprises about 49% weight based on the weight of the formulation.

In some embodiments, the ratio of the microemulsion component to the adhesive component is from about 95:5 to about 60:40. In other embodiments, the ratio of the microemulsion component to the adhesive component is from about 90:10 to about 70:30 or about 70:30 to about 51:49. In other embodiments, the ratio of the microemulsion component to the adhesive component is from about 85:15 to about 80:20, or from 80:20 to about 55:45. In other embodiments, the ratio of the microemulsion component to the adhesive component is from about 65:35 to about 55:45.

Acrylate-Based Polymers

In certain embodiments, the drug-containing layer of the present transdermal delivery system comprises one or more acrylates copolymers. In certain embodiments, the drug-containing layer comprises a carboxyl functional group containing acrylic-based polymer which is an acrylates copolymer. In certain embodiments, the drug-containing layer comprises a hydroxyl functional group containing acrylic-based polymer which is an acrylates copolymer.

Acrylate polymers may comprise copolymers of various monomers which may be "soft" monomers or "hard" monomers or combinations thereof. Soft monomers are characterized by having lower glass transition temperature. Examples of soft monomers include, but not limited to, n-butyl acrylate, 2-ethylhexyl acrylate and isooctyl acrylate. Hard monomers are characterized by having higher glass transition temperature. Examples of hard monomers include, but not limited to methyl methacrylate, ethyl acrylate and methyl acrylate. Soft monomers with lower glass transition temperature generally have higher solubility and better stability compared to hard monomers.

Monomers from which the acrylate polymers may be produced may comprise acrylic acid, methacrylic acid, butyl acrylate, butyl methacrylate, hexyl acrylate, hexyl methacrylate, isooctyl acrylate, isooctyl methacrylate, glycidyl methacrylate, 2-hydroxyethyl acrylate, methyl acrylate, methylmethacrylate, 2-ethylhexyl acrylate and 2-ethylhexyl methacrylate. Additional examples of acrylic adhesive monomers are described in Satas, "Acrylic Adhesives," Handbook of Pressure-Sensitive Adhesive Technology, 2nd ed., pp. 396-456 (D. Satas, ed.), Van Nostrand Reinhold, New York (1989).

Acrylate polymers may comprise bipolymer, terpolymer or tetrapolymer or copolymers of even greater numbers of monomers, including copolymers of alkyl acrylates, alkyl methacrylates, coploymerizable secondary monomers and/or monomers having functional groups.

In addition, the acrylic-based polymers may have hydroxyl functional group and/or carboxyl functional groups which can influence properties of the polymers such as solubility of clobazam, miscibility with other components of the transdermal patch as well as clobazam flux rate.

In certain embodiments, acrylic-based polymers having functional groups are copolymers or terpolymers which contain monomer units having functional groups. The monomers can be monofunctional or polyfunctional. These functional groups include carboxyl groups, hydroxy groups, amino groups, amido groups, epoxy groups, etc. In certain embodiments, the functional groups are carboxyl groups and hydroxy groups. In certain embodiments, the carboxyl functional monomers include acrylic acid, methacrylic acid, itaconic acid, maleic acid, and crotonic acid. In certain embodiments, the hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate.

In certain embodiments, these functional monomers are incorporated into the copolymer or terpolymer in an amount of 0.1 to 20% by weight, 0.1 to 4% by weight, 4 to 8% by weight, based on the dry weight of the total acrylic-based polymer.

In certain embodiments, the proportions of acrylic-based polymers also depend on the content of the functional monomer units in the functional acrylic. In certain embodiments, a composition will require less of a functional acrylic that contains 20% by weight of functional groups as opposed to one that contains 0.5% by weight of functional groups to achieve the same effect required for solubility and flux. In certain embodiments, the amount of functional acrylic is within the range of about 1 to 99 weight %, 1 to 5 weight %, 5 to 20 weight %, or 20 to 30 weight %, 30 to 65% weight %, 65 to 99% weight %, based on the total polymer content of the composition. In certain embodiments, the amount of non-functional acrylic or acrylic with a functional group which does not have as great of an affinity for the drug, is within the range of about 99 to 1 weight %, 95 to 75 weight %, 75 to 65 weight %, or 65 to 30 weight %, 30 to 20 weight %, based on the total polymer content of the composition.

The acrylic-based polymers may or may not contain cross-linkers that provide chemical bonds between polymer chains so as to mitigate cold flow within the transdermal patch of the present invention. In some embodiments, the cross-linkers comprise about 0.01% to about 6% by weight of the drug-containing layer. Examples of cross-linkers that may be used with acrylic-based polymers containing hydroxyl functional group include but are not limited to polybutyl titanate (PBT), tetrabutyl titanate (TBT), titanium dialkoxide bis(acetylacetonate) and/or titanium metal chelate. Examples of cross-linkers that may be used with acrylic-based polymers containing carboxyl functional group include but are not limited to aluminum tris (acetyl acetonate) and/or aluminium metal chelate. In addition, the acrylic-based polymers may be combined with tackifiers to provide adhesive property.

In certain embodiments, the carboxyl functional group containing acrylic-based polymer comprises an acrylate copolymer of 2-ethylhexyl acrylate, vinyl acetate, butyl acrylate, acrylic acid and a crosslinker.

In certain embodiments, the hydroxyl functional group containing acrylic-based polymer comprising an acrylate copolymer of 2-ethylhexyl acrylate, methyl acrylate and 2-hydroyxyethyl acrylate, or an acrylate copolymer of 2-ethylhexyl acrylate, vinyl acetate and 2-hydroxyethyl acrylate.

Examples of commercially available acrylic-based polymer that are acrylic-hydrocarbon hybrid polymers may be sourced from polymer solutions including, but not limited to, Duro-Tak™ 87-502B and Duro-Tak™ 87-504B, Duro-Tak™ 87-502A, Duro-Tak™ 87-503A and Duro-Tak™ 87-504A. Examples of acrylate-based polymers with no functional group may be sourced from polymer solutions including, but not limited to, Duro-Tak™ 87-4098, Duro-Tak™ 87-900A and Duro-Tak™ 87-9301. Examples of acrylate-based polymers having carboxyl functional group may be sourced from solutions including, but not limited to, Duro-Tak™ 87-235A (DT 235A), Duro-Tak™ 87-2353 (DT 2353), Duro-Tak™ 87-2852, Duro-Tak™ 87-2051, Duro-Tak™ 87-2052, Duro-Tak™ 87-2054 (DT 2054), Duro-Tak™ 87-2194 and Duro-Tak™ 87-2196. Examples of acrylate-based polymers having hydroxyl functional group may be sourced from solutions including, but not limited to Duro-Tak™ 87-2510 (DT 2510), Duro-Tak™ 87-2287, Duro-Tak™ 87-4287 and Duro-Tak™ 87-2516 (DT 2516). Examples of acrylate-based polymers having both hydroxyl and carboxyl functional groups may be sourced from solution including, but not limited to Duro-Tak™ 87-2074 and Duro-Tak™ 87-2979. In certain embodiment, the polymers are not Duro-Tak™ 387-2287, Duro-Tak™ 87-2287, Duro-Tak™ 87-900A, Duro-Tak™ 87-2194, Duro-Tak™ 287-2194 or Duro-Tak™ 87-2196.

In certain embodiments, the acrylic polymer is Duro-Tak™ 87-235A (DT 235A), Duro-Tak™ 87-4098 (D 4098), Duro-Tak™ 87-2510 (DT2510), Duro-Tak™ 87-9301 (DT9301), Duro-Tak™ 87-900A (DT900A), Duro-Tak™ 87-9088 (DT9088), and combinations thereof. In certain embodiments, the hydroxyl functional group containing acrylic-based polymer is Duro-Tak™ 87-2516 (DT 2516), Duro-Tak™ 87-2510 (DT 2510), or a combination thereof.

Exemplary acrylic-based polymers and their properties are listed in Table 1.

TABLE 1

| | | Typical Physical Properties | | | |
|---|---|---|---|---|---|
| Product | Description | Contains vinyl acetate | Contains Cross-linker | Solids (%) | Viscosity (cP or mPa · s) |
| Duro-Tak 87-900A | acrylates copolymer | No | n/a | 43 | 1800 |
| Duro-Tak 87-9301 | acrylates copolymer | No | n/a | 36.5 | 9500 |
| Duro-Tak 87-4098 | acrylates copolymer | Yes | n/a | 38.5 | 6500 |
| Duro-Tak 87-2510 | acrylates copolymer | No | No | 40.5 | 4250 |
| Duro-Tak 87-2287 | acrylates copolymer | Yes | No | 50.5 | 18000 |
| Duro-Tak 87-4287 | acrylates copolymer | Yes | No | 39 | 8000 |
| Duro-Tak 87-2516 | acrylates copolymer | Yes | Yes | 41.5 | 4350 |
| Duro-Tak 87-2074 | acrylates copolymer | No | Yes | 29.5 | 1500 |
| Duro-Tak 87-235A | acrylates copolymer | No | No | 36.5 | 8000 |
| Duro-Tak 87-2353 | acrylates copolymer | No | No | 36.5 | 8000 |
| Duro-Tak 87-2852 | acrylates copolymer | No | Yes | 33.5 | 2500 |
| Duro-Tak 87-2051 | acrylates copolymer | Yes | No | 51.5 | 4000 |
| Duro-Tak 87-2052 | acrylates copolymer | Yes | Yes | 47.5 | 2750 |
| Duro-Tak 87-2054 | acrylates copolymer | Yes | Yes | 47.5 | 2750 |
| Duro-Tak 87-2194 | acrylates copolymer | Yes | Yes | 45 | 3000 |
| Duro-Tak 87-2196 | acrylates copolymer | Yes | Yes | 45 | 2100 |
| Duro-Tak 87-2979 | acrylates copolymer | Yes | — | 44.5 | 2700 |
| Duro-Tak 87-2825 | acrylates copolymer | Yes | — | 47.5 | 1650 |
| Duro-Tak 87-2525 | acrylates copolymer | Yes | — | 41.5 | 4350 |

In certain embodiments, the adhesive is in an amount ranging from about 20% to about 25% by weight (wt %), from about 25% to about 30% by weight (wt %), from about 30% to about 35% by weight (wt %), from about 35% to about 40% by weight (wt %), from about 40% to about 45% by weight (wt %), from about 45% to about 50% by weight (wt %), from about 50% to about 55% by weight (wt %), from about 55% to about 60% by weight (wt %), from about 60% to about 65% by weight (wt %), from about 65% to about 70% by weight (wt %), from about 70% to about 75% by weight (wt %), or from about 75% to about 80% by weight (wt %), from about 80% to about 85% by weight (wt %), from about 85% to about 90% by weight (wt %), from about 90% to about 95% by weight (wt %), or from about 95% to about 99% by weight (wt %), relative to the total weight of the drug-containing layer (or the total weight of the composition).

Polymers

In certain embodiments, the drug-containing layer of the present transdermal patch further comprises one or more polymers for housing the active agent (e.g., clobazam or a pharmaceutically acceptable salt thereof) that play a significant role in determining clobazam flux rate. Specifically, higher flux rate may be achieved by lowering the solubility of the clobazam within the polymer(s) relative to the solubility within the stratum corenum layer of the user's skin. However, low solubility of clobazam may cause crystallization of clobazam within the skin patch, reducing the amount of clobazam available to be delivered to a user. In addition, low solubility of respective ingredients of the transdermal patch, or low miscibility, could present manufacturing issues as it could prevent even distribution of clobazam within the polymers and cause phase separation. Therefore, solubility of clobazam within the polymers and miscibility of respective components of the transdermal patch are considerations that necessitate proper balancing when selecting polymers and creating formulations using the selected polymers for the transdermal delivery system of the present disclosure.

In some non-limiting embodiments, the polymer is selected from the group consisting of cellulose ethers, methyl cellulose ethers, cellulose, hydroxylated cellulose, methyl cellulose, and hydroxylated methyl cellulose, gums selected from guar, locust, karaya, xanthan, gelatin, ethylcellulose (EC), vinylpyrrolidone-vinyl acetate copolymer (PVP-VA), polyvinylpyrrolidone (PVP), and derivatives thereof. In some embodiments, the polymer are hydroxypropyl cellulose (HPC), ethylcellulose (EC), vinylpyrrolidone-vinyl acetate copolymer (PVP-VA), polyvinylpyrrolidone (PVP).

Crystallization Inhibitor

In certain embodiments, the transdermal drug delivery system further comprises a crystallization inhibitor. In some non-limiting embodiments, the crystallization inhibitor may be selected from the group consisting of hydroxypropyl cellulose (HPC), hydroxyethyl cellulose (HEC), hydroxypropylmethylcellulose (HPMC), Copolymer, copolymers of methacrylic acid, polyvinylpyrrolidone (PVP) and its derivatives such as PVP K12; dextrin derivatives; polyethylene glycol (PEG); polypropylene glycol (PPG), polyvinyl alcohol (PVA), Poly(1-vinylpyrrolidone-co-Vinyl Acetate) (PVP/VA), and poloxamers. In one embodiment, the crystallization inhibitor is a poloxamer.

In certain embodiments, the crystallization inhibitor (or a combination of crystallization inhibitors) is in an amount ranging from about 0.5% to about 1% by weight (wt %), from about 1% to about 2% by weight (wt %), from about 2% to about 5% by weight (wt %), from about 15% to about 20% by weight (wt %), from about 20% to about 25% by weight (wt %), from about 25% to about 30% by weight (wt %), from about 30% to about 35% by weight (wt %), from about 35% to about 40% by weight (wt %), from about 40% to about 45% by weight (wt %), from about 45% to about 50% by weight (wt %), from about 50% to about 55% by weight (wt %), or from about 55% to about 60% by weight (wt %), relative to the total weight of the drug-containing layer (or the total weight of the composition).

5.4 Additional Layers

In some embodiment, the transdermal delivery system further comprises an intermediate adhesive layer comprising a second adhesive and optionally an enhancer, wherein the clobazam or a pharmaceutically acceptable salt thereof has a lower solubility in the intermediate adhesive layer than the drug-containing layer. In some embodiments, the intermediate adhesive layer is located between the drug-containing layer and the impermeable backing layer. In some embodiments, the second adhesive in the intermediate adhesive layer is the same as the adhesive in the drug-containing layer. In some embodiments, the second adhesive in the intermediate adhesive layer is different from the adhesive in the drug-containing layer.

The transdermal delivery device can further include an in-line adhesive at a position more proximal to the body surface than the clobazam-containing layer. Further, the in-line adhesive can be put in for rate-controlling function to reduce the flux through the body surface. For example, the in-line adhesive can be the body-contacting adhesive layer that is disposed on the body-facing side of the clobazam-containing layer. In certain embodiments, more layers can be disposed on the body proximal side of the clobazam-containing drug layer either before a rate-control layer or after the rate-control layer. In certain embodiments, the rate-control layer is the in-line body-contacting adhesive. Such a structure will facilitate the ease of making of the device, because fewer layers are included. The rate-control adhesive slows the flux of clobazam to a level that is suitable to deliver the drug at a therapeutically effective rate of greater than about 1-3 mcg/(cm$^2$ hr); about 3-5 mcg/(cm$^2$ hr), about 5-8 mcg/(cm$^2$ hr), about 10-30 mcg/(cm$^2$ hr), about 30-80 mcg/(cm$^2$ hr), about 8 mcg/(cm$^2$ hr) to 60 mcg/(cm$^2$ hr). Without the rate-control adhesive, the flux would have been higher, unless another rate limiting layer is used.

In one embodiment, the in-line, rate-control adhesive is made of a material that is different from the clobazam-containing layer. In one embodiment, the rate-control adhesive is made of polyisobutylene (PIB). PIB has excellent adhesive property and is suitable for retaining the device on body surface for 1-day delivery or multiple day delivery, i.e., 2-day, 3-day, etc., even up to 7-day delivery. PIB adhesives are mixtures of high molecular weight (HMW) PIB, low molecular weight (LMW) PIB, and/or plasticizer such as polybutene. Such mixtures are described in the art, e.g., U.S. Pat. No. 5,508,038. The molecular weight of the HMW PIB is usually in the range of about 700,000 to 2,500,000 Da, whereas that of the LMW PIB typically ranges from about 1,000 to about 90,000, about from 35,000 to 50,000. The molecular weights referred to herein are weight average molecular weights. The weight ratio of HMW PIB to LMW PIB in the adhesive ranges between about 1:1 to 1:20, preferably about 1:3 to 1:10. By adjusting the ratio of HMW and LMW PIB or using plasticizer, the rheological properties of the PIB adhesive can be tailored so that the desired adhesive properties can be achieved. Generally, higher amount of LMW PIB and the use of plasticizer will decrease modulus but increase cold flow.

In certain embodiments, the adhesive composition contains the HMW and LMW PIB in weight ratios (HMW PIB: LMW PIB) in the range of about 3-40:97-60, in the range of about 5-25:95-75 and in the range of about 10-20:90-80. The ratio of HMW PIE to LMW PIE that provides an optimal adhesive for a specific drug agent will be dependent upon the identity and concentration of agent being delivered. As an example, in one effective embodiment the PIB adhesive includes 5 wt % HMW PIB material (such as OPPANOL L80, L1OO, and L 140 from BASF) and 95 wt % LMW PIB material (Such as OPPANOL BlO, BI 1, B12, and B13 from BASF). Such an exemplary PIB adhesive 2-3 mil (0.05 mm to 0.075 mm) in thickness demonstrated rate-control when combined with a clobazam (35 wt %) in EVA40 (ethylene-vinyl acetate copolymer with 40% vinyl acetate, such as EL V AX® 4OW from DuPont) drug layer about 4-7 mil (0.1 to 0.175 mm) thick, resulting in clobazam base average flux of (5.5 µg/cm$^2$-h).

Optionally, modification of flux of the drug through the PIB can be effected by incorporating in the adhesive material such as micronized, crosslinked polyvinylpyrrolidone (PVP), such as CROSPOVIDONE (Kollidon CL-CY from BASF typically with bulk density between 0.2-0.3 g/cm3 and particle size D90 of 10-20 micron). Such PVP improves the permeability of clobazam material through the PIB layer. For example, the 5:95 L100:B12 PIB adhesive was formulated to include 20 wt % CROSPOVIDONE, from which an average clobazam base flux of 33.3µg/(cm$^2$-h) was achieved.

Varying the amounts of CROSPOVIDONE in the PIB adhesive would result in fine-tuning the flux of clobazam to desired levels. For example, multilaminate formulations containing different PVP amounts were tested for the effect of such variation on flux through skin. The multilaminate formulations contained 35 wt % of clobazam base in EVA40, an EVA12 as tie layer and PIB adhesive (5:95 L100:B12 PIB) with 12 wt % or 18 wt % PVP were tested. The formulation containing 12 wt % PVP resulted in a flux of 5.4µg/(cm$^2$ h) whereas that from the formulation containing 18 wt % PVP resulted in a flux of 7.5µg/(cm$^2$ h). A formulation containing 30 wt % clobazam base and 15 wt % PVP was also tested. The flux of clobazam formulation from this formulation was 6.3µg/(cm$^2$ h). This experiment indicated that the amount of PVP added in the PIB adhesive could be adjusted to change the flux of clobazam base to desired levels. PIB polymers are available commercially, e.g., under the tradename VISTANEX™ from Exxon Chemical. The amount of PVP in the resulting adhesive can be about 1 wt % to 30 wt %, about 5 wt % to 25 wt %, about 8 wt % to 20 wt %.

The term, "plasticizer" as used herein relating to PIB refers to compounds other than the agent being delivered, such as mineral oil, polybutene oil, and other low molecular weight hydrocarbons that act to plasticize PIB adhesives and increase their permeability to the agent being delivered. An adhesive composition is substantially free of plasticizer if it contains, at most, trace amounts of plasticizer and more preferably, no plasticizer. The term, "tackifier" as used herein relating to PIB refers to material, other than PIB, that is added to adhesives to increase their tack or stickiness. Such materials are typically naturally occurring resinous or resinous materials or synthetic polymer materials. An adhesive is substantially free of tackifier if it contains, at most, trace amounts of tackifier and preferably no tackifier.

The PIB can be with or without tackifiers or plasticizers, such as low molecular weight polybutene (e.g., INDOPOL H 1900 and/or high Tg, low molecular weight aliphatic resins such as the ESCOREZ resins available from Exxon Chemical, and the like). The body-contacting adhesive can be further modified to improve body surface adhesion. For example, a body-contacting adhesive containing 16 wt % L100 PIB, 24 wt % OPPANOL B12 PIB, 40 wt % INDOPOL H1900 polybutene, and 20 wt % CROSPOVIDONE will provide superior body surface adhesion and continue to provide rate-control. Rate-control can be further adjusted by adjusting the body-contacting adhesive thickness, for example, by increasing the adhesive thickness to provide greater rate-control.

The thickness of the in-line adhesive layer (which optionally can also be rate-controlling) will generally be from about 0.5 mil (0.127 mm) to 6 mil (0.154 mm), preferably about 2 mil (0.05 mm) to 3 mil (0.076 mm). Although it is desired that the adhesive functions in rate-control, the composition and thickness of the adhesive layer is provided such that the adhesive layer does not constitute a significant permeation barrier to the passage of the agent to be delivered but act adequately for rate-controlling function if rate-control is desired in the adhesive. PIB is particularly useful in this respect. Unless a drug requires the use of a loading dose to rapidly saturate drug delivery sites in the skin, the adhesive thickness is also preferably selected so that the adhesive does not contain a substantial amount of drug agent and preferably less than about 15 wt % of the total amount of the drug agent in the patch.

Yet another adhesive that can be used for in-line adhesive, which can be a body-contacting adhesive, is a polyacrylate (acrylic polymers), e.g., polyacrylate described in US patent publication US20040213832. A preferred type of polyacrylate is made from monomeric esters, preferably monomeric esters of alcohols that have 1 to 8 carbon atoms in the alcohol. Preferred alcohols include alkyl alcohol, hydroxyalkyl alcohol, methoxyalkyl alcohol and vinyl alcohol. A preferred monomeric ester has only one such 1 to 8 carbon atoms group from an alcohol and one organic group from an organic acid (e.g., acrylic acid and methacrylic acid). Examples of polyacrylate-based adhesives are as follows, identified as product numbers, manufactured by National Starch (Product Bulletin, 2000, DURO-TAK® is a trademark of National Starch adhesives): 87-4098, 87-2287, 87-4287, 87-2516, 87-2051, 87-2052, 87-2054, 87-2196, 87-9259, 87-9261, 87-2979, 87-2510, 87-2353, 87-2100, 87-2852, 87-2074, 87-2258, 87-9085, 87-9301 and 87-5298. DURO-TAK® 87-2287 and 87-4287 both are polymeric adhesives derived from monomer compositions that are similar: 5.2 wt % 2-hydroxy ethyl acrylate, about 20-40 wt % vinyl acetate, and about 55-75 wt % 2-ethylhexyl acrylate; and these two polymeric adhesives are provided solubilized in ethyl acetate in solids content of about 40-50 wt %. The DURO-TAK® 87-4287 monomeric components consist of the above-mentioned three monomeric esters. The DURO-TAK® 87-2287 adhesive is derived from monomeric components consisted of four monomers: vinyl acetate, 28%; 2-ethylhexyl acrylate, 67%; hydroxyethyl acrylate, 4.9%; and glycidyl methacrylate, 0.1%, see U.S. Pat. No. 5,693,335. In certain workable embodiments, the adhesive has little or no acid functionality. Preferably it is substantially free of an adhesive polymer of acrylic acid or (meth) acrylic acid. In such adhesives, there is little or no adhesive that is polymerized from monomeric components of acrylic acid or (meth) acrylic acid. For example, the adhesive can have 4 wt % or less of a polymer that is polymerized from acrylic acid or (meth) acrylic acid monomers. It is preferred that a polyacrylate adhesive be used with a rate-control tie layer such as EV A9 and/or EVA12, and/or EVAl 8.

Another kind of in-line body-contacting adhesive that can be used is a silicone adhesive. The silicone adhesives that may be used are typically high molecular weight poly dimethyl siloxanes or polydimethyldiphenyl siloxanes. Formulations of silicone adhesives that are useful in transdermal patches are described in U.S. Pat. Nos. 5,232,702, 4,906,169 and 4,951,622. One example of such a silicone adhesive is Silicone 4202 polydimethylsiloxane adhesive from Dow Corning. It is noted that other polysiloxane pressure sensitive adhesives can be used. Similar to the above in-line adhesives, the thickness can be adjusted by one skilled in the art based on whether the body-contacting adhesive is to have a rate-controlling function, in view of the present disclosure. EVA tie layer(s) can also be used with a silicone in-line body-contacting adhesive.

In certain embodiments, one or more tie layers can be included in the patch. To increase bonding of the EVA clobazam reservoir layer to the body-contacting adhesive (e.g., PIB) for secure attachment such that delamination can be prevented, the clobazam delivery device can include a tie-layer (or multiple layers if desired) of EVA with a vinyl acetate concentration less than that of the EVA in the clobazam reservoir layer, the vinyl acetate concentration being preferably about 8 wt % or more and less than about 40 wt %, preferably about 20 wt % or less, more preferably about 9 wt % to 20 wt %, even more preferably about 9 wt % to 18 wt % (e.g., adhesive EVA12), even more preferably about 9 wt % to 10 wt %. The reduced vinyl acetate content in the tie layer compared to the drug layer improves the tie layer's compatibility with the nonpolar PIB or other nonpolar or less polar adhesives and results in a stronger bond than if an EVA with a higher vinyl acetate content is used. Such a tie layer was found by peel testing to provide increased bond strength to prevent delamination. It has been demonstrated through in-vitro flux testing that permeation is restricted by the inclusion of a 1 mil (0.025 mm) EV A9 membrane between a clobazam reservoir layer (e.g., of EVA40) and a body-contacting adhesive (e.g., the PIB embodiments described above) more permeable than the EV A9. The use of a tie layer of a 1 mil (0.025 mm) EVA12 membrane or EVAl 8 membrane between a clobazam reservoir layer (e.g., of EVA40) and a highly permeable body-contacting adhesive did not affect the permeation significantly. The thickness of the tie layer is about 0.5 mil (0.0.0127 mm) to 5 mil (0.0625 mm), about 0.5 mil (0.0127 mm) to 2 mil (0.05 mm), about 0.5 mil (0.0127 mm) to 1 mil (0.0254 mm), about 1 mil (0.0254 mm) to 2 mil (0.05 mm). Minimized thickness in the tie layer and selection of a tie layer that has little rate-controlling function is preferred if it is desired to reduce risk of rate-control effect, if any, caused by the tie-layer. In certain embodiments, the material and the thickness of tie layer also contribute to the rate-controlling function, along with the rate-control adhesive (e.g., PIB).

Generally, an EVA tie layer is laminated to an EVA drug layer by heat pressing so that the tie layer and the drug layer fuse together. Adhesive is typically heat-cast on a separate carrier liner material. Then the EVA drug layer laminate and adhesive laminate are laminated together to obtain final product. Typically, the EVA drug layer is heat-cast on a carrier liner material first for easier processing as a laminate and then the laminate is further laminated with the tie layer by heat.

In certain embodiments, in-line body-contacting adhesive that has less rate-controlling function is used and depends on the rate-control function of the tie layer to control the rate of clobazam delivery. For example, if the skin-contacting adhesive allows higher flux levels, additional rate-control could be added by modifying the tie-layer with reduced vinyl acetate content (such as using an EVA9, having 9 wt % vinyl acetate) to reduce the drug transport rate. Further the tie-layer thickness can also be modified to affect the drug transport rate (thicker to reduce the transport, or thinner to increase the transport).

5.5 Flux Rate

In certain embodiments, the present transdermal delivery system is a daily clobazam transdermal patch, which provides a steady state flux rate at about 0.5 µg/cm²·hr and up to about 20 µg/cm²·hr as well as a lag time of less than about 8 hours.

In certain embodiments, the present transdermal delivery system may be about 150 cm² or less, about 120 cm² or less, about 100 cm² or less, about 80 cm² or less, about 60 cm² or less, about 40 cm² or less, about 5 cm² to about 120 cm², about 40 cm² to about 100 cm², or about 60 cm² to about 80 cm².

5.6 Additional Features of the Transdermal Delivery System

In one embodiment, the transdermal delivery system comprises a backing layer, a drug containing layer located on the skin (body surface) side of the backing layer, a body-contacting adhesive, and a peelable protective layer on the body side. Upon use, the protective layer is removed and the device is applied such that the body-contacting adhesive is applied to contact the body surface (e.g., skin). The body-contacting adhesive adheres securely to the body surface. The body-contacting adhesive can be included in the drug layer. Preferably, the whole drug-containing layer is a material that has the desired adhesive properties. In one embodiment, the adhesive provides good adhesive property to ensure that the device stays attached to the body surface over the desired period.

In one embodiment, the transdermal delivery system comprises a backing layer, a silicone layer with or without active ingredient, an active substance area, a contact adhesive area, and a release liner.

In another embodiment, the transdermal delivery system comprises a backing layer, a silicone layer with or without active ingredient, an active substance area, a rate controlling membrane, a contact adhesive area, and a release liner.

In another embodiment, the transdermal delivery system comprises a backing layer, an active substance area, a rate controlling membrane, a contact adhesive area, and a release liner.

In another embodiment, the transdermal delivery system comprises a backing layer, an active substance area, a contact adhesive area, and a release liner.

In one embodiment, the transdermal delivery system comprises a backing layer, a silicone layer with or without active ingredient, an active substance area, and a release liner.

In one embodiment, the transdermal delivery system comprises a backing layer, an active substance area, a rate controlling membrane, and a release liner.

In one embodiment, the transdermal delivery system comprises a peelable protective layer (or liner). In one embodiment, the protective layer is made of a polymeric material that is metallized. Examples of the polymeric materials include polyurethane, polyvinyl acetate, polyvinylidene chloride, polypropylene, polycarbonate, polystyrene, polyethylene, polyethylene terephthalate, polybutylene terephthalate, paper, and the like, and a combination thereof. In certain embodiments, the protective layer includes a siliconized polyester sheet.

The transdermal drug delivery system also may include a drug impermeable backing layer or film. In some embodiments, the backing layer is adjacent the drug-containing composition. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates.

The backing layer can be made with conventional materials. It may be formed from any material suitable for making transdermal delivery patches, such as a breathable or occlusive material including fabric or sheet, made of polyvinyl acetate, polyvinylidene chloride, polyethylene, polyurethane, polyester, EVA, polyethylene terephthalate (PET), polybutylene terephthalate, coated paper products, aluminum sheet and the like, or a combination thereof. In preferred embodiments, the backing layer includes low density polyethylene (LDPE) materials, medium density polyethylene (MDPE) materials or high density polyethylene (HDPE) materials, e.g., SARANEX (Dow Chemical, Midland, Mich.). The backing layer may be a monolithic or a multi-laminate layer. In preferred embodiments, the backing layer is a multilaminate layer including nonlinear LDPE layer/linear LDPE layer/nonlinear LDPE layer. A preferred backing material is a laminate of a thin occlusive PET or equivalent film tied to an EVA film. Preferably the EVA in the backing contains 20 wt % or less of vinyl acetate content, more preferably about 12 wt % of vinyl acetate. Preferably the vinyl acetate content is about similar or within 5 wt % of the vinyl content (in wt %) of the tie layer (if any). The backing layer can have a thickness of about 0.012 mm (0.5 mil) to 0.125 mm (5 mil); preferably about 0.025 mm (1 mil) to 0.1 mm (4 mil); more preferably about 0.0625 mm (1.5 mil) to 0.0875 mm (3.5 mil).

A typical backing material has a thickness in the range of 2 to 1000 micrometers. For example, 3M's Scotch Pak® 1012 or 9732 (a polyester film with an ethylene vinyl acetate copolymer heat seal layer), 9723 (a laminate of polyethylene and polyester), or CoTran 9720 (a polyethylene film) are useful in the transdermal drug delivery systems described herein, as are Dow® backing layer films, such as Dow® BLF 2050 (a multi-layer backing comprising ethylene vinyl acetate layers and an internal SARAN® layer.

A transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products of Dow Corning Corporation designated Bio-Release® liner and Syl-Off® 7610, Loparex's PET release liner (silicone-coated) and 3M's 1020, 1022, 9741, 9744, 9748, 9749 and 9755 Scotchpak™ (fluoropolymer-coated polyester films).

A transdermal drug delivery system may be packaged or provided in a package, such as a pouchstock material used in the prior art for transdermal drug delivery systems in general. For example, DuPont's Surlyn® can be used in a pouchstock material. Alternatively, a pouchstock comprising a coextruded ethylene acrylic acid/low-density polyethylene (EAA/LDPE) material, or Barex® from INEOS (acrylonitrile-methyl acrylate) may be used.

To further improve body surface adhesion, optionally, an overlay adhesive can also be used. Typically, an overlay is a layer of material positioned at the top (i.e., the side most distal from the body surface during application) of the device with adhesive on the body-proximal side of the overlay. The overlay has a size slightly larger in area than the drug-containing layer in the device (which as a patch has a generally flat configuration) such that there is a ring-shaped overhang (or border) of the overlay around the device for the adhesive on the overhang to adhere securely to the body surface. An overlay can have an aggressive body-contacting adhesive, such as one with 16 wt % L100 PIB, 24 wt % OPPANOL B 12 PIB, 40 wt % INDOPOL H 1900 polybutene, and 20 wt % CRO SPOVIDONE. This adhesive is applied to a backing material, such as the 3M SCHOTCH-PAK 9732 backing film previously described, or a nonwoven elastomeric backing material. The overlay adhesive is cut to be larger than the active component of the patch (as described above), for example 2 cm longer in each linear dimension for a rectangular patch, and 2 cm longer in diameter for a circular patch. The overlay is laminated into place over the active component of the patch during manufacturing, held in place by the adhesive, and centered so as to provide, in this example, a 1 cm border around the patch perimeter for improving adhesion security of the system on the body surface.

Transdermal flux can be measured with a standard procedure using Franz cells or using an array of formulations. Flux experiments were done on isolated human cadaver epidermis. With Franz cells, in each Franz diffusion cell a disc of epidermis is placed on the receptor compartment. A transdermal delivery system is placed over the diffusion area (1.98 $cm^2$) in the center of the receptor. The donor compartment is then added and clamped to the assembly. At time 0, receptor solution (between 21 cm and 24 ml, exactly measured) is added into the receptor compartment and the cell maintained at 35° C. This temperature yields a skin surface temperature of 30-32° C. Samples of the receptor compartment are taken periodically to determine the flux through skin and analyzed by HPLC. An alternative way to test flux is to use an array of patches. In testing flux with an array of transdermal miniature patches, formulations are prepared by mixing stock solutions of each of the mixture components of formulation in organic solvents (about 15 wt % solids), followed by a mixing process. The mixtures are then aliquoted onto arrays as 4-mm diameter drops and allowed to dry, leaving behind solid samples or "dots." (i.e., mini-patches). The miniature patches in the arrays are then tested individually for flux through skin using a permeation array, whose principle of drug flux from a patch formulation through epidermis to a compartment of receptor medium is similar to that of Franz cells (an array of miniature cells). The test array has a plurality of cells, a piece of isolated human epidermis large enough to cover the whole array, and a multiple well plate with wells acting as the receptor compartments filled with receptor medium. The assembled permeation arrays are stored at 32° C. and 60% relative humidity for the duration of the permeation experiments. Receptor fluid is auto-sampled from each of the permeation wells at regular intervals and then measured by HPLC to determine the flux of the drug.

A wide variety of materials that can be used for fabricating the various layers of the transdermal delivery patches of this invention have been described above. It is contemplated that materials other than those specifically disclosed herein, including those that may hereafter become known to the art to be capable of performing the necessary functions can be used by those skilled in the art.

5.7 Preparation of Transdermal Delivery System

The present transdermal delivery system (e.g., dermal patch) may be formulated in accordance with procedures disclosed in, e.g., US 2017/0049714, the disclosure of which is incorporated herein by reference.

In certain embodiments, the present transdermal patch may be made by (a) preparing an oily phase by mixing clobazam or a pharmaceutically acceptable salt thereof, an oily component and a solvent; (b) preparing a hydrophilic phase comprising a surfactant and optionally a permeation enhancer and/or a solubilizer; (c) adding to the oily phase and/or the hydrophilic phase one or more excipients selected from the group consisting of a permeation enhancer, a solubilizer and combinations thereof; (d) mixing the oily phase with the hydrophilic phase to obtain an oil-in-water microemulsion; (e) adding an adhesive and optionally a polymer to the microemulsion to obtain an adhesive composition; (f) providing an impermeable backing layer; and (g) applying the adhesive composition to the backing layer so as to obtain a transdermal drug delivery system.

5.8 Uses of Transdermal Delivery System

On application to the skin, the clobazam in the matrix of the patch diffuses into the skin where it is absorbed into the bloodstream to produce a systemic drug effect. The onset of the drug effect depends on various factors, such as, potency of the clobazam, the solubility and diffusivity of the clobazam in the skin, thickness of the skin, concentration of the clobazam within the skin application site, concentration of the clobazam in the matrix, and the like. In one embodiment, the present transdermal delivery system is kept on the skin for about 12 hours to about 24 hours, about 20 hours to about 24 hours, or about 24 hours to about 30 hours, without removal. Then a new transdermal delivery system of the present invention is applied soon after to minimize fluctuations in clobazam blood concentration.

The present disclosure provides methods and compositions (e.g., a transdermal patch, a topical composition, etc.) for treating or preventing diseases and conditions for which clobazam is indicated.

Thus, in some embodiment, the present disclosure relates to a method of treating or preventing seizure or related disorders. The method may comprise applying the present composition (e.g., a transdermal patch, a topical composition, etc.) to a subject (e.g., to an area of the skin of a subject).

In other embodiments, the present disclosure relates to a method of treating or preventing anxiety. The method may comprise applying the present composition (e.g., a transdermal patch, a topical composition, etc.) to a subject (e.g., to an area of the skin of a subject).

In other embodiments, the present disclosure relates to a method of treating or epilepsy. The method may comprise applying the present composition (e.g., a transdermal patch, a topical composition, etc.) to a subject (e.g., to an area of the skin of a subject).

5.9 Combination with Other Active Agents

The present dermal transdermal delivery system containing the active agent (e.g., clobazam, or a pharmaceutically acceptable salt, derivative, or solvate thereof) or composition may be administered (or applied) to the subject simultaneously with, before, after, or in a sequence and within a time interval of, the administration of a second active agent(s).

By co-administration it is meant either the administration of a single composition containing both the present agent (e.g., clobazam, or a pharmaceutically acceptable salt, derivative, or solvate thereof) and a second active agent(s), or the administration of the present agent and a second active agent(s) as separate compositions within short time periods.

The present dermal delivery system or composition can be combined and administered with a second active agent(s) in separate compositions. In certain embodiments, the separate compositions are administered simultaneously. In certain embodiments, the separate compositions are not administered simultaneously, such as, for example, in a sequential manner.

The present dermal delivery system or composition may be administered (or applied) to a subject alone, or may be administered (or applied) to a subject in combination with one or more other treatments/agents (a second agent).

In certain embodiments, the second agent is an agent in the treatment of seizure, schizoaffective disorder, and/or schizophreniform disorders.

In certain embodiments, the second agent is chlorpromazine, fluphenazine, haloperidol, loxapine, molindone, perphenazine, pimozide, sulpiride, thioridazine, trifluoperazine, clobazam, aripiprazole, asenapine, clozapine, iloperidone, olanzapine, quetiapine, risperidone, ziprasidone, or combinations thereof.

In certain embodiments, combination therapy means simultaneous administration of the compounds in the same composition, simultaneous administration of the compounds in separate compositions, or separate administration of the compounds (in separate compositions).

In certain embodiments, the second agent/treatment is used as adjunctive therapy to the present dermal delivery system or composition. In certain embodiments, the treatment includes a phase wherein treatment with the second agent/treatment takes place after treatment with the present dermal delivery system or composition has ceased. In certain embodiments, the treatment includes a phase where treatment with the present dermal delivery system or composition and treatment with the second agent/treatment overlap.

Combination therapy can be sequential or can be administered simultaneously. In either case, these drugs and/or therapies are said to be "co-administered." It is to be understood that "co-administered" does not necessarily mean that the drugs and/or therapies are administered in a combined form (i.e., they may be administered separately (e.g., as separate compositions or formulations) or together (e.g., in the same formulation or composition) to the same or different sites at the same or different times).

In certain embodiments, a subject is treated concurrently (or concomitantly) with the present dermal delivery system or composition and a second agent. In certain embodiments, a subject is treated initially with the present transdermal delivery system or composition, followed by cessation of the present transdermal delivery system or composition treatment and initiation of treatment with a second agent. In certain embodiments, the present transdermal delivery system or composition is used as an initial treatment, e.g., by administration of one, two or three doses, and a second agent is administered to prolong the effect of the present transdermal delivery system or composition, or alternatively, to boost the effect of the present transdermal delivery system or composition. A person of ordinary skill in the art will recognize that other variations of the presented schemes are possible, e.g., initiating treatment of a subject with the present transdermal delivery system or composition, followed by a period wherein the subject is treated with a second agent as adjunct therapy to the present compound or composition treatment, followed by cessation of the present compound or composition treatment.

The present compound and the other pharmaceutically active agent(s) may be administered together or separately and, when administered separately this may occur simultaneously or sequentially in any order. The amounts of the present compound and the other pharmaceutically active agent(s) and the relative timings of administration will be selected in order to achieve the desired combined therapeutic effect.

In various embodiments, the therapies (e.g., a transdermal delivery system or composition provided herein and a second agent in a combination therapy) are administered about 0 minutes to about 5 minutes apart, about 5 minutes to about 30 minutes apart, about 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 168 hours part. In certain embodiments, the therapies are administered no more than 24 hours apart or no more than 48 hours apart. In certain embodiments, two or more therapies are administered within the same patient visit. In other embodiments, the composition provided herein and the second agent are administered concurrently. In other embodiments, the composition provided herein and the second agent are administered at about 2 to 4 days apart, at about 4 to 6 days apart, at about 1 week part, at about 1 to 2 weeks apart, or more than 2 weeks apart. In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months. In certain embodiments, a composition provided herein and a second agent are administered to a subject in a sequence and within a time interval such that the composition provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the composition provided herein and the second active agent exerts their effect at times which overlap. Each second active agent can be administered separately, in any appropriate form and by any suitable route. In other embodiments, the composition provided herein is administered before, concurrently or after administration of the second active agent. In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the present agent/compound. In one embodiment, the composition provided herein is administered concurrently with one or more second agents in the same pharmaceutical composition. In another embodiment, a composition provided herein is administered concurrently with one or more second agents in separate pharmaceutical compositions. In still another embodiment, a composition provided herein is administered prior to or subsequent to administration of a second agent. Also contemplated are administration of a composition provided herein and a second agent by the same or different routes of administration, e.g., oral and parenteral. In certain embodiments, when the composition provided herein is administered concurrently with a second agent that potentially produces adverse side effects including, but not limited to, toxicity, the second active agent can advantageously be administered at a dose that falls below the threshold that the adverse side effect is elicited.

5.10 Dosing

The present transdermal delivery system or composition may be administered (or applied) once, twice, three times, four times, five times, six times or more per day, or as needed, during the course of treatment. In certain embodiments, the present transdermal delivery system or composition may be administered (or applied) at least once a day, at least twice a day, at least three times per day, or more. In certain embodiments, the present transdermal delivery system or composition may be administered (or applied) at least once a week, at least twice a week, at least three times a week, at least once per month, at least twice per month, or more frequently. Treatment can continue as long as needed. In one embodiment, the transdermal delivery system or composition may be administered (or applied) to a subject once daily.

The present transdermal delivery system or composition may be administered (or applied) daily, weekly, biweekly, several times daily, semi-weekly, every other day, bi-weekly, quarterly, several times per week, semi-weekly, monthly etc., to maintain an effective dosage level. The duration and frequency of treatment may depend upon the subject's response to treatment.

In certain embodiments, a subject may be administered 1 dose, 2 doses, 3 doses, 4 doses, 5 doses, 6 doses or more of the present composition. In certain embodiments, a single dose of the present agent/composition is administered in the present method. In certain embodiments, multiple doses of the present agent/composition (e.g., 2 doses, 3 doses, 4 doses, 5 doses, 6 doses, 7 doses, 8 doses, 9 doses, 10 doses or more) are administered in the present method. In one embodiment, each dose equates to a single patch.

In certain embodiments, the administration of the present agent/composition is continued over a period of up to 2 days, up to 3 days, up to 4 days, up to 5 days, up to 6 days, up to 1 week, up to 2 weeks, up to 3 weeks, up to 4 weeks, 2 weeks, 3 weeks, 4 weeks, 5 weeks, 6 weeks, 7 weeks, 8 weeks, 9 weeks, 10 weeks, or longer.

In certain embodiments, the present agent/composition is administered once, twice, at least twice, at least three times, at least four times, at least five time, at least six times, at least seven times, at least eight times, at least nine times, or more per treatment.

5.11 Subjects

The subject may be a human. In certain embodiments, the subject is a non-human animal. The non-human animal may be a mammal selected from the group comprising primates (non-human primates), pigs, rodents, or rabbits. In an embodiment, the subject is a pig, such as a miniswine. In another embodiment, the subject is a mouse.

5.12 Kits

The present disclosure also encompasses an article of manufacture, e.g., a kit. The article of manufacture may contain the present transdermal delivery system or composition in a suitable container with labeling and instructions for use. In certain embodiments, the container can be a dropper or tube with a suitable small orifice size, such as an extended tip tube made of any pharmaceutically suitable material. The topical formulations can be filled and packaged into a plastic squeeze bottle or tube. Optionally, an applicator can be provided in or attached to the container, or separately from the container.

Instructions may be packaged with the composition, for example, a pamphlet or package label. The labeling instructions explain how to the present composition, in an amount and for a period of time sufficient to treat or prevent the disorder or condition discussed herein. In certain embodiments, the label includes the dosage and administration instructions, the transdermal delivery system's or topical formulation's composition, the clinical pharmacology, drug resistance, pharmacokinetics, absorption, bioavailability, and/or contraindications.

5.13 Topical Administration

In certain embodiments, the present composition is formulated for topical administration. The terms "topically administrable composition," a "topical composition," or a "topical formulation," as used herein, refer to any formulation or composition which is pharmaceutically and/or cosmetically acceptable for topical delivery of the specified compounds of embodiments of the invention. The composition may be administered to a defined area of the body such as a defined area of skin surface or mucous membrane.

The present composition may additional contain a physiologically acceptable medium, such as a vehicle and/or a carrier. By "physiologically acceptable medium" is intended a cosmetically and/or dermatologically acceptable medium, which is compatible with the skin.

In some embodiments, the present composition can additionally include one or more pharmaceutically acceptable excipients. One of ordinary skill in the art would be familiar with pharmaceutically acceptable excipients. For example, the pharmaceutically acceptable excipient may be a water-soluble sugar, such as mannitol, sorbitol, fructose, glucose, lactose, and sucrose.

The present composition can be formulated in any pharmaceutical form normally provided for topical application to the skin, in particular formulated as solutions or dispersions of lotion or serum type, emulsions of liquid or semi-liquid consistency of the milk type, obtained by dispersion of a fatty phase in an aqueous phase (O/W) or, conversely, (W/O), or suspensions or emulsions of soft consistency of the aqueous or anhydrous cream or gel type, or, alternatively, microgranules, nanoparticles, microemulsions, nanocapsules, or vesicle dispersions of ionic and/or nonionic type.

Exemplary forms of formulation that can be used for topical administration include, but are not limited to, sprays, mists, aerosols, solutions, lotions, gels, serum, creams, ointments, pastes, unguents, emulsions and suspensions. The composition may be in the form of aqueous, aqueous/alcoholic or oily solutions, dispersions of lotion or serum type, aqueous anhydrous or lipophilic gels, emulsions of liquid or semi-liquid consistency of the milk type, obtained by dispersion of a fatty phase in an aqueous phase or conversely an aqueous phase in a fatty phase, or suspensions or emulsions of semi-solid or solid consistency of the cream or gel type, soaps or detergents, or alternatively microemulsions, microcapsules, microparticles, or vesicle dispersions of ionic and/or non-ionic type. Among additional alternative means for topical application of the compositions are spray pumps, aerosol dispersions, impregnated cosmetic facial masks, and impregnated cosmetic facial cloths or sponges.

In certain embodiments, the topically composition are prepared by mixing a pharmaceutically acceptable carrier with the present agent of known methods in the art, for example, methods provided by standard reference texts such as, Remington: The Science and Practice of Pharmacy 1577-1591, 1672-1673, 866-885 (Alfonso R. Gennaro ed. 19th ed. 1995); Ghosh, T. K.; et al. Transdermal and Topical Drug Delivery Systems (1997), both of which are hereby incorporated herein by reference.

The present composition may further contain a gelling agent, a polyol, a protective agent, a cosmetic agent, an adsorbent, a preservative, an antioxidant, a surfactant, a skin-penetration agent, a local anesthetic, an analgesic etc.

Suitable gelling agents known in the art, including those used in the two-phase or single-phase gel systems, can be used in the present invention. Some examples of suitable gelling agents are disclosed in Remington: The Science and Practice of Pharmacy 1517-1518 (Alfonso R. Gennaro ed. 19th ed. 1995), which is hereby incorporated herein by reference. The gelling agents include, but are not limited to, one or more hydrophilic and hydroalcoholic gelling agents used in the cosmetic and pharmaceutical industries. Non-limiting examples of gelling agents include hydroxyethylcellulose, cellulose gum, MVE/MA decadiene crosspolymer, PVM/MA copolymer, glycerine polyacrylate, or a combination thereof. Exemplary hydrophilic gelling agents include carboxyvinyl polymers (carbomer), acrylic copolymers such as acrylate/alkylacrylate copolymers, polyacrylamides, polysaccharides such as hydroxypropylcellulose, natural gums and clays, and, exemplary lipophilic gelling agents include modified clays such as bentones, metal salts of fatty acids such as aluminum stearates, and hydrophobic silica. Exemplary hydrophilic active agents are proteins or protein hydrolysates, amino acids, polyols, urea, allantoin, sugars and sugar derivatives, vitamins and hydroxy acids.

Polyols in gel formulations can serve one or more functions such as solubilizing agents, moisturizers, emollients, skin humectant, skin-penetration agents, etc. Suitable polyols that can be used in embodiments of the present invention include, but are not limited to, glycerine, propylene glycol, dipropylene glycol, hexylene glycol, butylene glycol, and liquid polyethylene glycols, such as polyethylene glycol 200 to 600. Other et al., Gels and Jellies, pp. 1327-1344 of Encyclopedia of Pharmaceutical Technology, vol. 3 (ed. by Swarbrick, et al, pub. by Marcel Dekker, 2002); or Pena, "Gel Dosage Forms: Theory, Formulation, and Processing," pp. 381-388 of Topical Drug Delivery Formulations, (ed. by Osborne et al., pub. by Marcel Dekker, Inc., 1990).

Suitable preservatives include, but are not limited to, quaternary ammonium compounds, such as benzalkonium chloride, benzethonium chloride, cetrimide, dequalinium chloride, and cetylpyridinium chloride; alcoholic agents, for example, chlorobutanol, phenylethyl alcohol, and benzyl alcohol; parabens such as methylparaben, ethylparaben, propylparaben, and butylparaben; antibacterial esters, for example, esters of parahydroxybenzoic acid; and other antimicrobial agents such as chlorhexidine, chlorocresol, benzoic acid, polymyxin, and phenoxyethanol. Preferably, the preservative is selected from the group consisting of sodium benzoate, phenoxyethanol, benzyl alcohol, methylparaben, imidazolidinyl urea and diazolidinyl urea.

Topical administration can continue for about 1 day, about 2 days, about 3 days, about 4 days, about 5 days, about 6 days, about 7 days, about 2 weeks, about 3 weeks, about 4 weeks, about 2 months, about 3 months, about 4 months, about 5 months, about 6 months, about 1 year or longer.

In some embodiments, the present composition may comprise one or more pharmaceutically acceptable buffering agents. Any pharmaceutically acceptable buffering agent known to those of ordinary skill in the art is contemplated for inclusion in the present pharmaceutical compositions. Examples of such buffering agents include of monobasic sodium phosphate, dibasic sodium phosphate, sodium benzoate, potassium benzoate, sodium citrate, sodium acetate, and sodium tartrate.

The pH of the topical formulations may be within a physiologically acceptable pH, e.g., within the range of about 4 to about 8, of about 6 to about 7.5, or about 4.5 to 6.5.

In some embodiments, the topical formulations may contain moisturizing agents. Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturization factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

This invention will be better understood from the following examples. However, one skilled in the art will readily appreciate that the specific methods and results discussed are merely illustrative and not limiting.

6. EXAMPLES

Example 6.1—Solubility Studies

Solubility and compatibility of clobazam were tested in a variety of excipients according to the following functions:

(1) alcohols; (2) emollients/oils; (3) esters; (4) fatty acids; (5) fatty acid esters; (6) fatty alcohols; (7) solubilizers; (8) solvents; and (9) surfactants. It was found that clobazam has good solubility in 4-allyl-2-ethoxyphenol among various alcohols. Clobazam also has good solubility in methyl L-lactate, levulinic acid and ethyl levulinate among various fatty acids and fatty acid esters. Clobazam has some solubility in Caprylocaproyl polyoxyl-8 glycerides and transcutol P among various surfactants, polymers and oils. Clobazam has good solubility in dichloromethane (DCM), chloroform, dimethylacetamide (DMA), 1,3-dimethyl-2-imidazolidinone (DMI), dimethylsulfoxide (DMSO) and N-methylpyrrolidone (NMP).

Ingredients for different phases of the microemulsion of the present disclosure were selected based on clobazam solubility, as described in Example 6.2

Example 6.2—Microemulsion Preparation

Based on solubility experiments in Example 6.1, the following microemulsion phase ingredients were selected, as depicted in Table 1:

TABLE 1

| Hydrophilic Phase | Solvent/Co-Solvent Phase | Surfactant/Co-Surfactant | Oil Phase |
|---|---|---|---|
| Benzyl alcohol | Dimethyl sulfoxide (DMSO) | Medium chain triglycerides | 4-allyl-2-ethoxyphenol |
| PEG-400 | 1,3-dimethyl-2-imidazolidinone (DMI) | Sorbitan Monooleate (Span 80) | Levulinic acid |
| Ethyl levulinate | Acrylic acid | Diethylene glycol monoethyl ether | Lactic Acid |
| Triacetine | N-methylpyrrolidone (NMP) | Propylene glycol monolaurate | Peg-6 caprylic/capric glycerides |

TABLE 1-continued

| Hydrophilic Phase | Solvent/Co-Solvent Phase | Surfactant/Co-Surfactant | Oil Phase |
|---|---|---|---|
| Tetraethylene glycol | Dimethylacetamide (DMA) | Oleoyl polyoxyl-6 glycerides | Sodium lauryl sulfoacetate (and) disodium laureth sulfosuccinate |
| Propylene glycol | | Propylene glycol monocaprylate | 2-Phenoxyethanol |
| | | Caprylocaproyl polyoxyl-8 glycerides | Oleic acid |
| | | Tween-20 Glyceryl caprylate Glycerol monocaprylate Macrogolglycerol hydroxystearate | Oleyl Alcohol |

An exemplary microemulsion comprising clobazam or a pharmaceutically acceptable salt thereof, a hydrophilic phase, a solvent/co-solvent, a surfactant/co-surfactant and an oil phase was prepared as follows: a solution of surfactant and cosurfactant was mixed in a solution of clobazam or clobazam salt, oil and co-solvent. An oil/in-water (o/w) microemulsion thus formed. The composition of exemplary microemulsions are shown in Table 2.

Hydrophilic phase is the aqueous phase in this case, as the microemulsion is mixed with the acrylic adhesives, no water is added in the formulation; therefore, the aqueous phase was replaced by a hydrophilic phase. Each phase was tested to find the best combination and searched for combination to combine the four different phases to form microemulsion with good clobazam solubility. For example, for the hydrophilic phase, we found H8, H10 and H11 have the best solubility for clobazam. Below are some examples of the hydrophilic phase and solvent/co-solvent phase:

| Hydrophilic Phase | H1 | H2 | H3 | H4 | H5 | H6 | H7 | H8 | H9 | H10 | H11 | H12 | H13 | H14 | H15 |
|---|---|---|---|---|---|---|---|---|---|---|---|---|---|---|---|
| Benzyl alcohol | 1 | 1 | 1 | 1 | | | | 3 | | 3 | 3 | 3 | 3 | 3 | 2 |
| PEG-400 | 2 | 2 | 1 | 1 | 1 | 2 | 1 | 1 | 2 | | | 1 | 2 | | 1 |
| Ethyl levulinate | 2 | 1 | 2 | 1 | 2 | 2 | 2 | 1 | 1 | 2 | 1 | | | | 2 |
| Triacetine | | 1 | 1 | 2 | 2 | 1 | 2 | | 2 | | 1 | 1 | | 2 | |

| | Co-solvent phase | | | | | | | | | | | | | | |
|---|---|---|---|---|---|---|---|---|---|---|---|---|---|---|---|
| Solvent | A1 | A2 | A3 | A4 | A5 | A6 | A7 | A8 | A9 | A10 | A11 | A12 | A13 | A14 | A15 |
| DMSO | 1 | 1 | 1 | 1 | | | | | | | | | | 1 | 1 |
| DMI | 2 | 2 | 1 | 1 | 1 | 2 | 1 | 1 | 2 | | | 1 | 2 | | 1 |
| Acrylic acid | 2 | 1 | 2 | 1 | 2 | 2 | 2 | 1 | 1 | 2 | 3 | 3 | 3 | 3 | 3 |
| NMP | | 1 | 1 | 2 | 2 | 1 | 2 | 3 | 2 | 3 | 2 | 1 | | 1 | |

Each individual phase were mixed together first.
For example: in the hydrophilic phase, using H8 as an example: 3 parts of Benzyl alcohol, 1 part of PEG-400 and 1 part of Ethyl levulinate were mixed; using H10 as an example: 3 parts of Benzyl alcohol, and 2 parts of Ethyl levulinate were mixed.
In the solvent/Co-Solvent case: Using A8 as an example: 1 part of DMI, 1 part of acrylic acid, and 3 parts of NMP were mixed. Same for the surfactant and co-surfactant phase and oil phase.

Each possible combination is prepared by adding 35, 45, or 30 part of hydrophilic phase, 20 or 25 part of solvent and co-solvent phase, 15 or 30 part of surfactant and co-surfactant phase and 5, 10 or 15 part of oil phase. The solubility of clobazam at different combination were determined as shown in Table 6 to 8.

Exemplary hydrophilic (H), solvent/cosolvent (A), surfactant/co-surfactant (S) and oily phase (O) were prepared according to Tables 3-6 below:

TABLE 2

Examples of components in the Hydrophilic phase

| Hydrophilic Phase | H1 | H2 | H3 | H4 | H5 | H6 | H7 | H8 | H9 | H10 | H11 | H12 | H13 | H14 | H15 |
|---|---|---|---|---|---|---|---|---|---|---|---|---|---|---|---|
| Benzyl alcohol | 1 | 1 | 1 | 1 | | | | 3 | | 3 | 3 | 3 | 3 | 3 | 2 |
| PEG-400 | 2 | 2 | 1 | 1 | 1 | 2 | 1 | 1 | 2 | | | 1 | 2 | | 1 |
| Ethyl levulinate | 2 | 1 | 2 | 1 | 2 | 2 | 2 | 1 | 1 | 2 | 1 | | | | 2 |
| Triacetine | | 1 | 1 | 2 | 2 | 1 | 2 | | 2 | | 1 | 1 | | 2 | |

TABLE 3

Example of components in the Solvent-Co-solvent Phase

| | Co-solvent phase | | | | | | | | | | | | | | |
|---|---|---|---|---|---|---|---|---|---|---|---|---|---|---|---|
| Solvent | A1 | A2 | A3 | A4 | A5 | A6 | A7 | A8 | A9 | A10 | A11 | A12 | A13 | A14 | A15 |
| DMSO | 1 | 1 | 1 | 1 | | | | | | | | | | 1 | 1 |
| DMI | 2 | 2 | 1 | 1 | 1 | 2 | 1 | 1 | 2 | | | 1 | 2 | | 1 |
| Acrylic acid | 2 | 1 | 2 | 1 | 2 | 2 | 2 | 1 | 1 | 2 | 3 | 3 | 3 | 3 | 3 |
| NMP | | 1 | 1 | 2 | 2 | 1 | 2 | 3 | 2 | 3 | 2 | 1 | | 1 | |

TABLE 4

Example of components in the surfactant-co-surfactant phase

| | Co-surfactant Phase | | | | | | | | | | | | | | |
|---|---|---|---|---|---|---|---|---|---|---|---|---|---|---|---|
| Surfactant | S1 | S2 | S3 | S4 | S5 | S6 | S7 | S8 | S9 | S10 | S11 | S12 | S13 | S14 | S15 |
| Medium chain triglycerides | 1 | 1 | 2 | | | | | 1 | 1 | | | | | | 1 |
| Span 80 | 2 | 1 | 2 | 1 | | | | | 1 | | | | 1 | 1 | |
| Diethylene glycol monoethyl ether | 2 | 2 | 1 | 1 | | | | | | | 1 | 2 | 1 | | 1 |
| Propylene glycol monolaurate | | 1 | | 1 | 2 | 1 | | | | | 2 | 1 | 1 | 1 | |
| Oleoyl polyoxyl-6 glycerides | | | | 2 | 1 | 1 | | 2 | | | 1 | | | | 1 |
| Propylene glycol monocaprylate | | | | | 2 | 1 | 2 | 1 | | 1 | | | 1 | 2 | |
| Caprylocaproyl polyoxyl-8 glycerides | | | | | | 1 | 1 | 1 | 2 | 1 | 1 | 1 | 1 | | 2 |
| Tween-20 | | | | | 1 | 2 | 1 | 2 | 1 | | | 1 | | 1 | |

TABLE 5

| Oily phase | O1 | O2 | O3 | O4 | O5 | O6 | O7 | O8 | O9 | O10 | O11 | O12 | O13 | O14 | O15 |
|---|---|---|---|---|---|---|---|---|---|---|---|---|---|---|---|
| 4-allyl-2-ethoxyphenol | 1 | 1 | 1 | 1 | | | | | | | | | | 1 | 1 |
| Levulinic acid | 2 | 2 | 1 | 1 | 1 | 2 | 1 | 1 | 2 | | | 1 | 2 | | 1 |
| Peg-6 caprylic/capric glycerides | | 1 | 1 | 2 | 2 | 1 | 2 | 3 | 2 | 3 | 2 | 1 | | 1 | |

TABLE 5-continued

| Oily phase | O1 | O2 | O3 | O4 | O5 | O6 | O7 | O8 | O9 | O10 | O11 | O12 | O13 | O14 | O15 |
|---|---|---|---|---|---|---|---|---|---|---|---|---|---|---|---|
| Sodium lauryl sulfoacetate (and) disodium laureth sulfosuccinate | 1 | | 1 | | 1 | 1 | | | | | 1 | 2 | 2 | 1 | 2 |

TABLE 6

| Example | Hydrophilic Phase 35% | Solvent/Co-Solvent 25% | Surfactant/Co-surfactant 15% | Oil Phase 15% | Clobazam Solubility (mg/mL) |
|---|---|---|---|---|---|
| 1 | H8 | A8 | S12 | O1 | 108.3 |
| 2 | H10 | A8 | S12 | O1 | 109.8 |
| 3 | H11 | A8 | S12 | O1 | 115 |
| 4 | H8 | A8 | S7 | O1 | 104.1 |
| 5 | H10 | A8 | S7 | O1 | 98.6 |
| 6 | H11 | A8 | S7 | O1 | 107.5 |
| 7 | H10 | A8 | S12 | O2 | 112.16 |
| 8 | H10 | A10 | S12 | O2 | 120.75 |
| 9 | H11 | A10 | S12 | O2 | 117.58 |
| 10 | H10 | A10 | S7 | O2 | 118.43 |
| 11 | H11 | A10 | S7 | O2 | 117.15 |

TABLE 7

| Example | Hydrophilic Phase 30% | Solvent/Co-Solvent 25% | Surfactant/Co-surfactant 30% | Oil Phase 5% | Clobazam Solubility (mg/mL) |
|---|---|---|---|---|---|
| 12 | H10 | A8 | S12 | O2 | 100.83 |
| 13 | H11 | A8 | S12 | O1 | 99.72 |
| 14 | H10 | A8 | S7 | O2 | 98.55 |
| 15 | H11 | A8 | S7 | O1 | 93.20 |

TABLE 8

| Example | Hydrophilic Phase 45% | Solvent/Co-Solvent 20% | Surfactant/Co-surfactant 15% | Oil Phase 10% | Clobazam Solubility (mg/mL) |
|---|---|---|---|---|---|
| 16 | H10 | A8 | S12 | O2 | 115.50 |
| 17 | H11 | A8 | S12 | O1 | 110.83 |
| 18 | H10 | A8 | S7 | O2 | 116.59 |
| 19 | H11 | A8 | S7 | O1 | 114.53 |

Example 6.3—In Vitro Skin Permeation Studies—Microemulsion

Various microemulsion were tested in a 4 days permeation study through human cadaver skin. The tested formulations are provided in Table 9 and 10.

TABLE 9

| | Composition % wt/wt | | |
|---|---|---|---|
| Ingredients | Ex. 20 | Ex. 21 | Ex. 22 |
| Clobazam | 5 | 5 | 5 |
| Diethylene glycol monoethyl ether | 20 | 20 | 20 |
| Triacetine | 10 | 10 | |
| Caprylocaproyl polyoxyl-8 glycerides | 5 | 5 | 5 |
| DMSO | 15 | 15 | 15 |
| DMI | 10 | 10 | 10 |
| Propylene glycol monolaurate | 10 | 10 | 10 |
| Tween 20 | 5 | 5 | 5 |
| Propylene glycol | 12 | | 12 |
| Phenoxyethanol | | | 10 |
| Tetraethylene glycol | | 12 | |
| Levulinic Acid | 5 | | |
| Lactid Acid | | 5 | 5 |
| $HPC_L$ | 3 | 3 | 3 |
| % release at 26 hr | 6% | 6% | 8% |
| Flux (μg/cm² hr) | 7.5 | 6.5 | 7.3 |

TABLE 10

| | Composition % wt/wt | | |
|---|---|---|---|
| Ingredients | Ex. 23 | Ex. 24 | Ex. 25 |
| Clobazam | 5 | 5 | 5 |
| DMA | 20 | 20 | 20 |
| Phenoxyethanol | 10 | 10 | 10 |
| DMSO | 15 | 15 | 15 |
| DMI | 10 | 10 | 10 |
| Tetra Ethylene Glycol | 12 | 12 | 12 |
| Lactid Acid | 5 | 5 | 5 |
| Tween 20 | 5 | 5 | 5 |
| Caprylocaproyl polyoxyl-8 glycerides | 5 | 5 | |
| Macrogolglycerol hydroxystearate | | | 5 |
| Glycerol Monocaprylate | 10 | | |
| Glyceryl caprylate | | 10 | |
| Propylene glycol monolaurate | | | 10 |
| $HPC_L$ | 3 | 3 | 3 |
| % release at 26 hr | 10% | 4% | 7% |
| Flux (μg/cm² hr) | 7.3 | 6.2 | 8.2 |

Example 6.4—Preparation of Microemulsion Films

Various microemulsions according to Example 6.2 and 6.3 were combined with adhesives, with or without polymers. The compositions are listed in Table 11-12 below:

TABLE 11

| | Composition % wt/wt | | |
|---|---|---|---|
| Ingredients | Ex 26 | Ex 27 | Ex 28 |
| Clobazam | 6.0 | 6.0 | 6.0 |
| DMI | 3.0 | 3.0 | 3.0 |
| Acrylic acid | 3.0 | 3.0 | 3.0 |
| NMP | 9.0 | 9.0 | 9.0 |

TABLE 11-continued

| | Composition % wt/wt | | |
|---|---|---|---|
| Ingredients | Ex 26 | Ex 27 | Ex 28 |
| Levulinic acid | 4.5 | 4.5 | 4.5 |
| Sodium lauryl sulfoacetate (and) disodium laureth sulfosuccinate | 2.3 | 2.3 | 2.3 |
| 4-allyl-2-ethoxyphenol | 2.3 | 2.3 | 2.3 |
| Benzyl alcohol | 12.6 | 12.6 | 12.6 |
| Ethyl levulinate | 8.4 | 8.4 | 8.4 |
| Poloxamer188 | 0.5 | 0.5 | 0.5 |
| Propylene glycol monocaprylate | 3.6 | 3.6 | 3.6 |
| Caprylocaproyl polyoxyl-8 glycerides | 1.8 | 1.8 | 1.8 |
| Tween-20 | 3.6 | 3.6 | 3.6 |
| Duro-Tak 87-235A | 39.5 | | |
| Duro-Tak 87-4098 | | 39.5 | |
| Duro-Tak 87-2510 | | | 39.5 |
| Observation | Film formed properly, free of crystallization | Film formed properly, free of crystallization | Film formed, but not tacky |

TABLE 12

| | Composition % wt/wt | | | |
|---|---|---|---|---|
| Ingredients | Ex 29 | Ex 30 | Ex 31 | Ex 32 |
| Clobazam | 5.0 | 5.0 | 5.0 | 5.0 |
| Transcutol P | 14.0 | 14.0 | 14.0 | 14.0 |
| Triacetine | 7.0 | 7.0 | 7.0 | 7.0 |
| Caprylocaproyl polyoxyl-8 glycerides | 3.4 | 3.4 | 3.4 | 3.4 |
| DMSO | 10.0 | 10.0 | 10.0 | 10.0 |
| DMI | 6.9 | 6.9 | 6.9 | 6.9 |
| PG | 8.0 | 8.0 | 8.0 | 8.0 |
| Lactid Acid | 3.4 | 3.4 | 3.4 | 3.4 |
| Propylene glycol monolaurate | 6.9 | 6.9 | 6.9 | 6.9 |
| Tween 20 | 3.4 | 3.4 | 3.4 | 3.4 |
| HPC L | 2.0 | 2.0 | 2.0 | 2.0 |
| EC N10 | 30.0 | | | |
| Methocel E15 | | 30.0 | | |
| Kollidon VA64 F | | | 30.0 | |
| Plasdone K90 | | | | 30.0 |
| % release at 26 hr | 13 | 12 | 8 | 5 |
| Flux ($\mu g/cm^2$ hr) | 2.0 | 1.7 | 2.0 | 2.0 |
| Observation | Film formed properly, free of crystallization | Film formed properly, free of crystallization | Film formed properly, free of crystallization | Film formed properly, free of crystallization |

As demonstrated in Table 11-12, several compositions of the present disclosures efficiently formed films that were free of crystallization.

Example 6.5—In Vitro Skin Permeation Studies—Multiple Layers

Various multiple layer patches were tested in a 4 days permeation study through human cadaver skin. The tested formulations are provided in Table 13-16. The preparation of the multiple layers:
Drug Layer: the ingredients were dissolved and coated as described previously.
Contact Adhesive layer: the ingredients were dissolved, coated, and dried as described previously.
Lamination and Die-Cut: A polypropylene microporous membrane such as Celgard® 2400, 3500 or Reemay® 2250 was laminated on the adhesive side of the contact adhesive layer. The drug layer was laminated on top of the rate controlling membrane, and the release liner on the drug layer was replaced with a backing film. The final five layer laminated was die-cut into transdermal patches.

TABLE 13

| Ex 33 | Composition % wt/wt | |
|---|---|---|
| Ingredients | Drug Layer | Contact Adhesive Layer |
| Clobazam | 5.5 | |
| Ethyl Levulinate | 13.7 | 20 |
| 2-phenoxyethanol | 6.8 | 10 |
| Macrogolglycerol hydroxystearate | 3.4 | 5 |
| DMSO | 10.2 | 10 |
| DMI | 6.8 | |
| Propylene Glycol | 6.1 | |
| Lactid Acid | 3.4 | 5 |
| Propylene glycol monolaurate | 6.8 | |
| Tween 20 | 3.4 | |
| $HPC_H$ | 2.0 | |
| Ethanol | 28.2 | |
| Poly(acrylic acid) | 3.5 | |
| Duro-Tal 87-4098 | | 50 |

TABLE 14

| Ex 34 | Composition % wt/wt | |
|---|---|---|
| Ingredients | Drug Layer | Contact Adhesive Layer |
| Clobazam | 5.9 | 20 |
| Ethyl Levulinate | 14.6 | 10 |
| 2-phenoxyethanol | 7.3 | 5 |
| Macrogolglycerol hydroxystearate | 3.7 | 10 |
| DMSO | 11.0 | — |
| DMI | 7.3 | — |
| Propylene Glycol | 6.6 | 5 |
| Lactid Acid | 3.7 | — |
| Propylene glycol monolaurate | 7.3 | — |
| Tween 20 | 3.7 | — |
| $HPC_H$ | 2.2 | — |
| Ethanol | 23.0 | — |
| Poly(acrylic acid) | 3.8 | 50 |
| Duro-Tal 87-4098 | — | 20 |

TABLE 15

| Ex 35 | Composition % wt/wt | |
|---|---|---|
| Ingredients | Drug Layer | Contact Adhesive Layer |
| Clobazam | 5.5 | — |
| Ethyl Levulinate | 13.7 | 20 |
| 2-phenoxyethanol | 6.8 | 10 |
| Macrogolglycerol hydroxystearate | 3.4 | 5 |
| DMSO | 10.2 | 10 |
| DMI | 6.8 | — |
| Propylene Glycol | 6.1 | — |
| Lactid Acid | 3.4 | 5 |
| Propylene glycol monolaurate | 6.8 | — |
| Tween 20 | 3.4 | — |
| $HPC_H$ | 2.0 | — |
| Ethanol | 28.2 | 40 |
| Poly(acrylic acid) | 3.5 | 10 |

TABLE 16

| Ex 36 | Composition % wt/wt | |
|---|---|---|
| Ingredients | Drug Layer | Contact Adhesive Layer |
| Clobazam | 5.9 | — |
| Ethyl Levulinate | 14.6 | 20 |
| 2-phenoxyethanol | 7.3 | 10 |
| Macrogolglycerol hydroxystearate | 3.7 | 5 |
| DMSO | 11.0 | 10 |
| DMI | 7.3 | — |
| Propylene Glycol | 6.6 | — |
| Lactid Acid | 3.7 | 5 |
| Propylene glycol monolaurate | 7.3 | — |
| Tween 20 | 3.7 | — |
| HPC$_H$ | 2.2 | — |
| Ethanol | 23.0 | 40 |
| Poly(acrylic acid) | 3.8 | 10 |

Example 6.6—In Vitro Skin Permeation Studies—Effects of Adhesives

Various adhesives were tested in a 3 days permeation study through human cadaver skin. The tested formulations are provided in Table 11.

TABLE 17

| | Composition % wt/wt | | | |
|---|---|---|---|---|
| Ingredients | Ex 37 | Ex 38 | Ex 39 | Ex 40 |
| Clobazam | 3.5 | 3.5 | 3.5 | 3.5 |
| Diethylene glycol monoethyl ether | 14 | 14 | 14 | 14 |
| Triacetine | 7 | 7 | 7 | 7 |
| Caprylocaproyl polyoxyl-8 glycerides | 3.5 | 3.5 | 3.5 | 3.5 |
| DMSO | 10.5 | 10.5 | 10.5 | 10.5 |
| DMI | 7 | 7 | 7 | 7 |
| Propylene glycol | 8.4 | 8.4 | 8.4 | 8.4 |
| Lactic Acid | 3.5 | 3.5 | 3.5 | 3.5 |
| Propylene glycol monolaurate | 7 | 7 | 7 | 7 |
| Tween 20 | 3.5 | 3.5 | 3.5 | 3.5 |
| HPC$_L$ | 2.1 | 2.1 | 2.1 | 2.1 |
| Duro Tak 87-4098 | 30 | | | |
| Duro Tak 87-9301 | | 30 | | |
| Duro Tak 87-900A | | | 30 | |
| Duro Tak 87-9088 | | | | 30 |
| % release at 27 hr | 4% | 10% | 6% | 11% |
| Observation | Free of Crystallization | Free of Crystallization | Free of Crystallization | Free of Crystallization |

Figure 1:
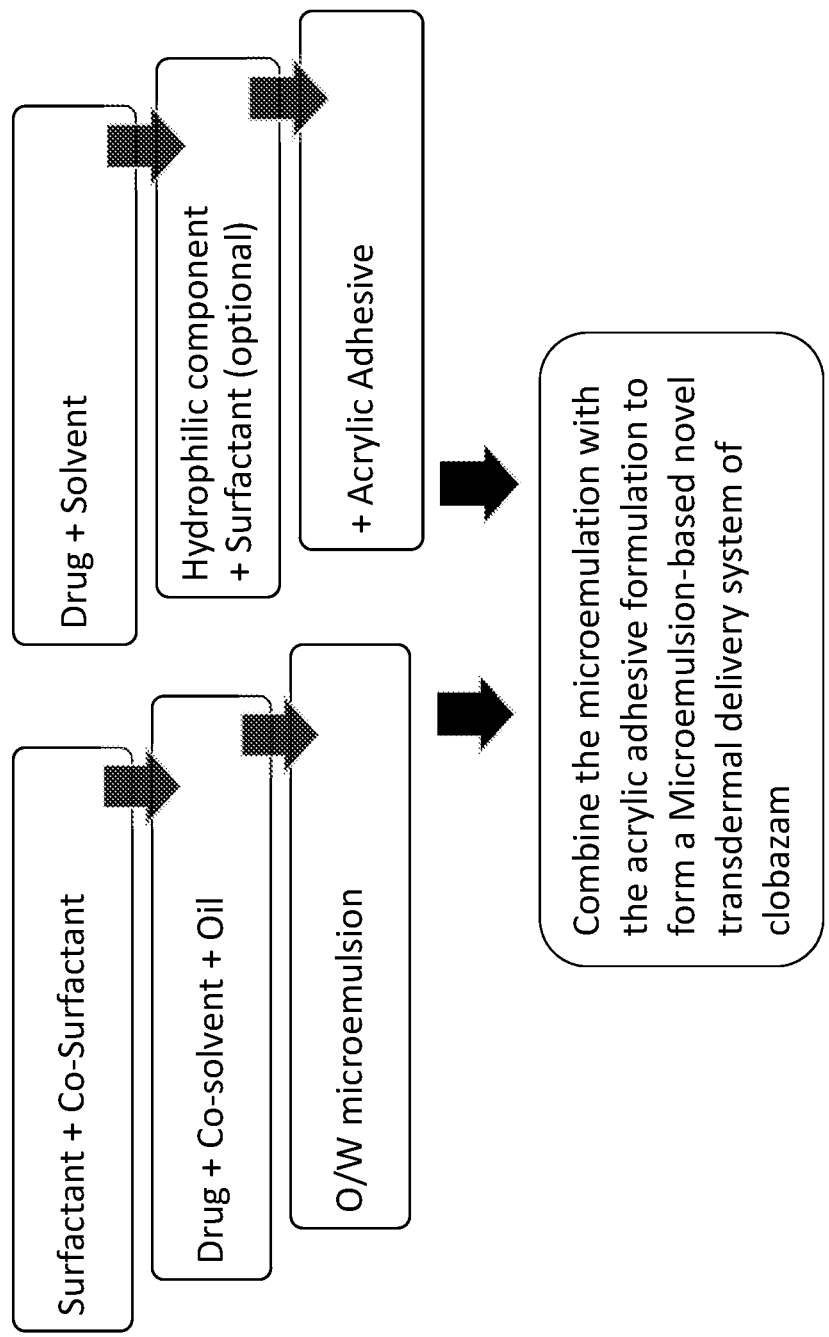
FIG. 1 shows a schematic process for preparing the transdermal delivery systems according to the present disclosure.
Figure 2:
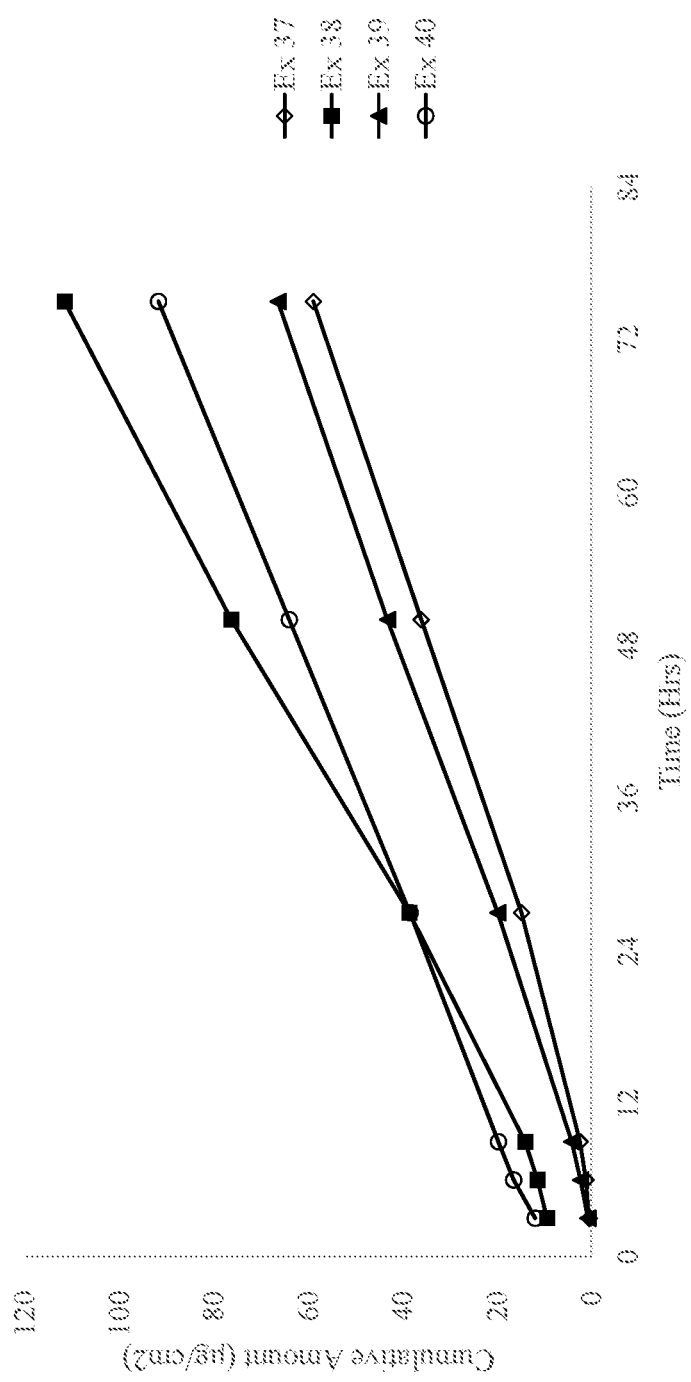
FIG. 2 shows clobazam release from the transdermal delivery (TDD) matrix system through human cadaver skin as a function of different adhesives. ◇=Example 37 (Duro TAK 87-4098); ■=Example 38 (Duro Tak 87-9301); ▲=Example 39 (Duro Tak 87-900A); ○=Example 40 (Duro Tak 87-9088).

The results were shown in FIG. 2. The permeation of Duro-Tak 87-9301 (DT9301) with non-functional groups provides very good results. DT 4098, 900A and 9088 also have very good results.

Example 6.5—In Vitro Skin Permeation Studies—Effect of Polymers

In these experiments, polymers of different molecular weights were added, and the formulations were tested in a 3 days permeation study through human cadaver skin. The tested formulations are provided in Tables 12 and 13.

TABLE 18

| | Composition % wt/wt | | |
|---|---|---|---|
| Ingredient | Ex 41 | Ex 42 | Ex 43 |
| Clobazam | 3.5 | 3.5 | 3.5 |
| Diethylene glycol monoethyl ether | 14 | 14 | 14 |
| Triacetine | 7 | 7 | 7 |
| Caprylocaproyl polyoxyl-8 glycerides | 3.5 | 3.5 | 3.5 |
| DMSO | 10.5 | 10.5 | 10.5 |
| DMI | 7 | 7 | 7 |
| Propylene glycol | 8.4 | 8.4 | 8.4 |
| Lactic Acid | 3.5 | 3.5 | 3.5 |
| Propylene glycol monolaurate | 7 | 7 | 7 |
| Tween 20 | 3.5 | 3.5 | 3.5 |
| HPC$_L$ | — | 2.1 | — |
| Klucel$_{HF}$ | — | — | 2.1 |
| Duro Tak 87-4098 | 30 | 30 | 30 |
| % release at 26 hr | 30% | 30% | 15% |
| Observation | Free of Crystallization | Free of Crystallization | Free of Crystallization |

As seen in Table 12 and FIG. 3, formulations with low substituted hydroxypropyl cellulose (HPC$_L$) or high molecular weight (1,150,000) hydroxypropylcellulose (Klucel$_{HF}$) efficiently formed films that were free of crystallization, and had good penetration properties, with Ex. 5 (HPC$_L$) exhibiting the best penetration properties.

TABLE 19

| | Composition % wt/wt | | |
|---|---|---|---|
| Ingredients | Ex. 44 | Ex. 45 | Ex. 46 |
| Clobazam | 4.8 | 4.8 | 4.8 |
| Diethylene glycol monoethyl ether | 16 | 16 | 16 |
| Triacetine | 9 | 9 | 9 |
| Caprylocaproyl polyoxyl-8 glycerides | 4 | 4 | 4 |
| DMSO | 12 | 12 | 12 |
| DMI | 8 | 8 | 8 |
| Propylene glycol | 9.6 | 9.6 | 9.6 |
| Lactic Acid | 4 | 4 | 4 |
| Propylene glycol monolaurate | 8 | 8 | 8 |
| Tween 20 | 4 | 4 | 4 |
| Oleic Acid | 1 | 1 | 1 |
| Oleyl Alcohol | 2 | 2 | 2 |
| HPC$_L$ | 2.4 | | |
| HPC$_{EF}$ | | 2.4 | |
| HPC$_{SSL}$ | | | 2.4 |
| Duro-Tak 87-4098 | 15.2 | 15.2 | 15.2 |
| % release at 26 hr | 15% | 6% | 6% |
| Observation | Free of Crystallization | Free of Crystallization | Free of Crystallization |

As seen in Table 13 and FIG. 4, formulations with low substituted HPC (HPC$_L$), HPC$_{EF}$ (age MW: 80,000), and low viscosity HPC$_{SSL}$ efficiently formed films that were free of crystallization and had good penetration properties, with Ex. 7 (HPC$_L$) exhibiting the best penetration properties.

TABLE 20

| | Composition % wt/wt | | |
|---|---|---|---|
| Ingredients | Ex. 47 | Ex. 48 | Ex. 49 |
| Clobazam | 10 | 10 | 11 |
| 2-phenoxyethanol | 20 | 20 | 19 |

TABLE 20-continued

| Ingredients | Composition % wt/wt | | |
|---|---|---|---|
| | Ex. 47 | Ex. 48 | Ex. 49 |
| Macrogol 15 Hydroxystearate | 5 | 4 | 4 |
| Levulinic Acid | 20 | 20 | 19 |
| Pyruvic Acid | 5 | 5 | 10 |
| DMI | 5 | 5 | 5 |
| Phenyl Acetate | 13 | 13 | 10 |
| Propylene glycol monolaurate | 5 | 5 | 5 |
| $HPC_H$ | 2 | 3 | 2 |
| Poly(acrylic acid) | 15 | 15 | 15 |
| % release at 98 hr | 9.4% | 9.3% | 9.7% |
| Observation | Free of Crystallization | Free of Crystallization | Free of Crystallization |

Example 6.5—In Vivo in Minipig

TABLE 21

| Ingredients | Composition % wt/wt | | |
|---|---|---|---|
| | Ex. 50 | Ex. 51 (Matrix Layer) | Ex. 51 (Contact Layer) |
| Clobazam | 4 | 7.6 | |
| Sodium lauryl sulfoacetate (and) disodium laureth sulfosuccinate | 55 | | |
| Macrogolglycerol hydroxystearate | 11 | 4.8 | 5 |
| Ethyl Levulinate | | 19.0 | 20 |
| 2-phenoxyethanol | | 9.5 | 10 |
| DMSO | | 14.3 | 10 |
| DMI | | 9.5 | |
| Propylene Glycol | | 8.6 | |
| Lactid Acid | | 4.8 | 5 |
| Propylene glycol monolaurat | | 9.5 | |
| Tween 20 | | 4.8 | |
| $HPC_H$ | | 2.9 | |
| Poly(acrylic acid) | | 4.7 | |
| Duro Tak 87-4098 | 30 | | 50 |
| Observation | Free of Crystallization | Free of Crystallization | |
| Stability of the Patch 40° C. for 1 month | <1% | <1% | |

Clobazam formulations produced in Table 21 were applied to Lanyu 400 minipig to assess the systemic bioavailability of Clobazam from the patch together with the local and systemic tolerance of the device and compare to the oral formulation taken twice daily at 20 mg. The patch was applied to the back of the minipig for a period of 4 days (96 hours) and the blood samples taken during the period of application. The results are shown in Table 22 and in FIG. 9. The data in FIG. 9 are the plasma level of Clobazam obtained by taking samples from the minipig at the predetermined time and analyzed by LC-MS.

TABLE 22

| Lanyu 400 Minipig | Ex 50 (n = 3) | Ex 51 (n = 3) | Oral |
|---|---|---|---|
| $AUC_{(0-t)}$ (h ng/mL) | 1117 ± 540 | 1687 ± 472 | 749 ± 704 |
| Irritation score (Drazie Scoring Scale) | 0/3 No edema 0/3 No erythema | 0/3 No edema 0/3 No erythema | n/a n/a |

The study demonstrated the sustained bioavailability of Clobazam via a transdermal patch. The patch demonstrated low dermal irritation potential and acceptable adhesiveness. The Clobazam patch was safe and well tolerated in all minipigs, both locally and systemically.

Exemplary systems and methods are set out in the following items:

Item 1a. A transdermal drug delivery system comprising:
(a) a drug-containing layer comprising:
(i) an oil-in-water microemulsion comprising: an oily phase comprising clobazam or a pharmaceutically acceptable salt thereof, an oily component and a solvent; and a hydrophilic phase comprising a surfactant, the microemulsion further comprising at least one of a permeation enhancer and/or a solubilizer; and
(ii) an adhesive component comprising a first adhesive, wherein the adhesive component comprises between about 5% and less than about 40% of the drug-containing layer; and
(b) an impermeable backing layer.

Item 1b. A transdermal patch comprising:
a. 10 to 90% w/w of microemulsion phase;
b. 0.1% to 40% w/w of adhesive;
c. 0.1 to 10% w/w of a crystallization inhibitor; and
d. a physiologically effective amount of clobazam loaded in the microemulsion phase, wherein the clobazam content of said patch remains substantially free of crystals when stored at 25° C. for at least four weeks.

Item 2a. The transdermal patch of any preceding item, wherein the microemulsion phase is an oil-in-water microemulsion comprising: (i) an oily phase comprising clobazam or a pharmaceutically acceptable salt thereof, an oily component and a solvent; (ii) a hydrophilic phase comprising a surfactant, and (iii) at least one permeation enhancer and/or a solubilizer.

Item 2b. The transdermal drug delivery system of any preceding item, wherein the oily component comprises one or more oils selected from the group consisting of aromatic oils, mineral oils, plant oils, animal oils, synthetic oils, silicone oils, fluoro oils, and any combination thereof.

Item 3. The transdermal drug delivery system of any preceding item, wherein the oily phase further comprises one or more excipients selected from the group consisting of alkyl benzoates, carboxylic acids, surfactants, emulsifiers, ketone and alcohol functional group and any combination thereof.

Item 4. The transdermal drug delivery system of any preceding item, wherein the oily phase comprises 4-allyl-2-ethoxyphenol levulinic acid, lactic acid, Peg-6 caprylic/capric glycerides, pyruvic acid, and/or Sodium lauryl sulfoacetate (and) disodium laureth sulfosuccinate.

Item 5. The transdermal drug delivery system of any preceding item, wherein the hydrophilic phase comprises at least one excipient selected from the group consisting of alcohol, ketone group, phenoxy ethanol, phenyl acetate, glycols, esters, and any combination thereof.

Item 6. The transdermal drug delivery system of any preceding item, wherein the hydrophilic phase comprises benzyl alcohol, polyethylene glycol, ethyl levulinate, and/or triacetin.

Item 7. The transdermal drug delivery system of any preceding item, wherein the microemulsion comprises a permeation enhancer selected from the group consisting of aliphatic alcohols, fatty acids having chain of 4 to 20 carbons, fatty acid esters, alcohol amines, polyhydric alcohol alkyl ethers, polyoxyethylene alkyl ethers, glycerides, middle-chain fatty acid esters of polyhydric alcohols having chain of 8-20 carbon atoms, alkyl esters having chain of 1-6 carbon atoms, acylated amino acids, pyrrolidone, pyrrolidone derivatives, and ethoxylated fatty alcohols.

Item 8. The transdermal drug delivery system of any preceding item, wherein the permeation enhancer is selected from the group consisting of Medium chain triglycerides, diethylene glycol monoethyl ether, Propylene glycol monolaurate, Oleoyl polyoxyl-6 glycerides, Propylene glycol monocaprylate and caprylocaproyl polyoxyl-8 glycerides.

Item 9. The transdermal delivery system of any preceding item, wherein the microemulsion comprises a solubilizer selected from the group consisting of polysorbate, span, surfactants, propylene glycol monocaprylate and its derivatives, glycols and its derivatives, triglycerides and its derivatives, diethylene glycol monoethyl ether, cyclodextrins, polyhydric alcohol, polyethylene glycol, tetrahydrofurfuryl alcohol, diethyl tolumide, monoisopropylidene glycerine, sulfoxides, and similar chemicals such as but not limited to dimethylsulfoxide, dimethylacetamide, dimethylformamide, decylmethylsulfoxide, dimethylisosorbide, Caprylocaproyl polyoxyl-8 glycerides, triacetine, and combinations thereof.

Item 10. The transdermal drug delivery system of any preceding item, wherein the solvent is selected from the group consisting of C1-C20 alcohols, polyhydric alcohols, isopropyl myristate, glycols selected from the group consisting of propylene glycol, polyethylene glycol, dipropylene glycol and hexylene glycol; glycerin, imidazolidinones, 1,3-dimethyl-2-imidazolidinone (DMI), pyrrolidones selected from the group consisting of N-methyl 2-pyrrolidone (NMP), 2-pyrrolidone; sulfoxides selected from the group consisting of dimethyl sulfoxide and decyl methyl sulfoxide; dimethyl isosorbide, mineral oils, vegetable oils, and carboxylic acids selected from the group consisting of acrylic acid, lactic acid and acetic acid.

Item 11. The transdermal drug delivery system of any preceding item, wherein the solvent comprises dimethyl sulfoxide (DMSO), 1,3-dimethyl-2-imidazolidinone (DMI), phenoxy ethanol, phenyl acetate, acrylic acid and/or NMP.

Item 12. The transdermal drug delivery system of any preceding item, wherein the surfactant is selected from the group consisting of an anionic surfactant, a cationic surfactant, a zwitterionic surfactant, a nonionic surfactant, and mixtures thereof.

Item 13. The transdermal drug delivery system of any preceding item, wherein the surfactant is selected from the group consisting of sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80 (Tween)), kolliphor derivates (macrogol ester) sodium lauryl sulfate, sorbitan esters selected form the group consisting of sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate and sorbitan tri-isostearate, lecithin pharmaceutical acceptable salts thereof and combinations thereof.

Item 14. The transdermal drug delivery system of any preceding item, further comprising a crystallization inhibitor.

Item 15. The transdermal drug delivery system of any preceding item, wherein the crystallization inhibitor is selected from the group consisting of cellulose ethers, methyl cellulose ethers, cellulose, hydroxylated cellulose, methyl cellulose, and hydroxylated methyl cellulose, gums selected from guar, locust, karaya, xanthan, gelatin, and derivatives thereof.

Item 16. The transdermal drug delivery system of any preceding item, wherein the crystallization inhibitor is a polymer selected from the group consisting of hydroxypropyl cellulose (HPC), hydroxyethyl cellulose (HEC), hydroxypropylmethyl cellulose (HPMC), copolymers of methacrylic acid, polyvinylpyrrolidone (PVP) and its derivatives; polyvinylpyrrolidone/vinyl acetate (PVP/VA) copolymer, dextrin derivatives; polyethylene glycol (PEG); polypropylene glycol (PPG), polyvinyl alcohol (PVA), and poloxamers.

Item 17. The transdermal drug delivery system of any preceding item, wherein the crystallization inhibitor is a poloxamer.

Item 18. The transdermal drug delivery system of any preceding item, wherein the crystallization inhibitor is hydroxypropyl cellulose (HPC).

Item 19. The transdermal delivery system of any preceding item, wherein the crystallization inhibitor comprises between about 1% to about 5% by weight (wt %) of total weight of the composition.

Item 20. The transdermal drug delivery system of any preceding item, wherein the adhesive component comprises first adhesive, the first adhesive comprising a polymer based on acrylic acid and its esters, isobutylenes, ethylene-vinyl acetate copolymers, natural rubbers, synthetic rubbers, styrene-diene copolymers, styrene-butadiene block copolymers, isoprene block copolymers, acrylonitrile-butadiene rubber, butyl rubber and neoprene rubber, pressure sensitive adhesives based on silicone, hot-melt adhesive, mixtures of esters of hydrogenated colophony with cellulose derivatives, and combinations thereof.

Item 21. The transdermal drug delivery system of any preceding item, wherein the adhesive component comprises an acrylic-based polymer.

Item 22. The transdermal drug delivery system of any preceding item, wherein the acrylic-based polymer contains more than 1% of the poly acrylic monomer.

Item 23. The transdermal drug delivery system of any preceding item, wherein the oil-in water microemulsion comprises:
 a. clobazam or a pharmaceutically acceptable salt thereof,
 b. an excipient selected from the group consisting of Labrafac™, Span, Transcutol P, Laurylglycol FCC, Labrafil, Propylene glycol monocaprylate, Caprylocaproyl polyoxyl-8 Glycerides®, Tween-20, and any combination thereof;
 c. an oily phase selected from the group consisting of 4-allyl-2-ethoxyphenol, Levulinic acid, Lactic Acid, Peg-6 caprylic/capric glycerides, Sodium lauryl sulfoacetate (and) disodium laureth sulfosuccinate, pyruvic acid, and any combination thereof;
 d. a hydrophilic phase selected from the group consisting of benzyl alcohol, polyethylene glycol, ethyl levulinate, phenoxy ethanol, phenyl acetate, and/or triacetine; and
 e. a solvent/co-solvent selected from the group consisting of DMSO, DMI, acrylic acid, NMP and any combination thereof.

Item 24. The transdermal drug delivery system of any preceding item, in the form of a transdermal patch.

Item 25. The transdermal drug delivery system of any preceding item, wherein the ratio of the microemulsion component to the adhesive component is from about 90:10 to about 60:40.

Item 26. The transdermal drug delivery system of any preceding item, wherein the ratio of the microemulsion component to the adhesive component is from about 70:30 to about 51:49.

Item 27. The transdermal drug delivery system of any preceding item, wherein the microemulsion comprises clobazam or a pharmaceutically acceptable salt thereof in an amount from about 1% to about 15% by weight (wt %) relative to total weight of the microemulsion.

Item 28. The transdermal drug delivery system of any preceding item, wherein the microemulsion comprises clobazam or a pharmaceutically acceptable salt thereof in an amount from about 5% to about 10% by weight (wt %) relative to total weight of the microemulsion.

Item 29. The transdermal drug delivery system of any preceding item, wherein the hydrophilic phase comprises between about 25% to about 50% by weight (wt %) of the total weight of microemulsion.

Item 30. The transdermal drug delivery system of any preceding item, wherein the oily phase comprises between about 1% to about 20% by weight (wt %) of the total weight of microemulsion.

Item 31. The transdermal drug delivery system of any preceding item, wherein the solvent comprises between about 15% to about 30% by weight (wt %) of the total weight of microemulsion.

Item 32. The transdermal drug delivery system of any preceding item, wherein the surfactant comprises between about 10% to about 40% by weight (wt %) of the total weight of microemulsion.

Item 33. The transdermal drug delivery system of any preceding item, wherein the microemulsion comprises between about 50% to about 90% by weight (wt %) of the total weight of the composition.

Item 34. The transdermal delivery system of any preceding item, wherein the drug-containing layer further comprises an antioxidant.

Item 35. The transdermal delivery system of any preceding item, further comprising an intermediate adhesive layer comprising a second adhesive and optionally an enhancer, wherein the clobazam or a pharmaceutically acceptable salt thereof has a lower solubility in the intermediate adhesive layer than the drug-containing layer.

Item 36. The transdermal delivery system of any preceding item, wherein the intermediate adhesive layer is located between the drug-containing layer and the impermeable backing layer.

Item 37. The transdermal delivery system of any preceding item, wherein the second adhesive in the intermediate adhesive layer is the same as the adhesive in the drug-containing layer.

Item 38. The transdermal delivery system of any preceding item, wherein the second adhesive in the intermediate adhesive layer is different from the adhesive in the drug-containing layer.

Item 39. The transdermal delivery system of any preceding item, which provides a flux rate of about 0.5 µg/cm²·hr to about 20 µg/cm²·hr for more than 24 hours.

Item 40. A method for treating or preventing epilepsy, anxiety, LGS or related disorders comprising the step of applying the transdermal delivery system according to any one of the preceding item s to a subject in need thereof.

Item 41. The method of any preceding item, wherein the transdermal delivery system is a patch that is applied to the subject for more than 24 hours, 1-2 days, 2-3 days, 3-4 days, 4-5 days, or 5-7 days.

Item 42. The method of any preceding item, wherein about 5 mg to about 80 mg of clobazam is delivered from the transdermal delivery system to the human subject daily.

Item 43. The method of item, wherein the transdermal delivery delivers 10-80 mg/day of clobazam to a subject.

Item 44. The method of any preceding item, wherein the subject achieves at least 150 ng/ml plasma concentration of clobazam about 2-24 hours after administration of the patch.

Item 45. A method of preparing a transdermal drug delivery system for administration of clobazam or a pharmaceutically acceptable salt thereof, the method comprising the step of:
  a. preparing an oily phase by mixing clobazam or a pharmaceutically acceptable salt thereof, an oily component and a solvent;
  b. preparing a hydrophilic phase comprising a surfactant;
  c. adding to the oily phase and/or the hydrophilic phase one or more excipients selected from the group consisting of a permeation enhancer, a solubilizer and combinations thereof;
  d. mixing the oily phase with the hydrophilic phase to obtain an oil-in-water microemulsion;
  e. adding an adhesive and optionally a polymer to the microemulsion to obtain an adhesive composition;
  f. providing an impermeable backing layer; and
  g. applying the adhesive composition to the backing layer so as to obtain a transdermal drug delivery system.

Item 46. A transdermal drug delivery system comprising:
  (a) a drug-containing layer comprising:
    (i) an oil-in-water microemulsion comprising: an oily phase comprising clobazam or a pharmaceutically acceptable salt thereof, an oily component and a solvent; and a hydrophilic phase comprising a surfactant, the microemulsion further comprising at least one of a permeation enhancer and/or a solubilizer; and
    (ii) an adhesive component comprising a first adhesive, wherein the adhesive component comprises between about 10% and less than about 50% of the drug-containing layer;
  (b) an impermeable backing layer;
  (c) an intermediate backing layer comprising a second adhesive, wherein the clobazam or a pharmaceutically acceptable salt thereof has a lower solubility in the intermediate adhesive layer than the drug-containing layer;
  (d) optionally, a releasing membrane layer;
  (e) optionally, a contact adhesive layer; and
  (f) a release liner layer.

Item 47. The transdermal delivery system according to any preceding item, wherein the drug-containing layer is in the form of a polymer matrix combined with a pressure sensitive adhesive system, a microemulsion combined with a pressure-sensitive adhesive system, a drug with enhancer layer combined with a pressure sensitive adhesive system, or a hydrogel.

Item 48. The transdermal patch according to any preceding item, wherein the oily component comprises one or more oils selected from the group consisting of aromatic oils, mineral oils, plant oils, animal oils, synthetic oils, silicone oils, fluoro oils, and any combination thereof.

Item 49. The transdermal patch according to any preceding item, wherein the oily phase further comprises one or more excipients selected from the group consisting of alkyl benzoates, carboxylic acids, surfactants, emulsifiers, ketone and alcohol functional group and any combination thereof.

Item 50. The transdermal patch according to any preceding item, wherein the hydrophilic phase comprises at least one excipient selected from the group consisting of alcohol, ketone group, glycols, esters, and any combination thereof.

Item 51. The transdermal patch according to any preceding item, wherein the permeation enhancer selected from the group consisting of aliphatic alcohols, fatty acids having chain of 4 to 20 carbons, fatty acid esters, alcohol amines, polyhydric alcohol alkyl ethers, polyoxyethylene alkyl ethers, glycerides, middle-chain fatty acid esters of polyhydric alcohols having chain of 8-20 carbon atoms, alkyl esters having chain of 1-6 carbon atoms, acylated amino acids, pyrrolidone, pyrrolidone derivatives, and ethoxylated fatty alcohols.

Item 52. The transdermal patch according to any preceding item, wherein the solubilizer selected from the group consisting of polysorbate, span, surfactants, propylene glycol monocaprylate and its derivatives, glycols and its derivatives, triglycerides and its derivatives, diethylene glycol monoethyl ether, cyclodextrins, polyhydric alcohol, polyethylene glycol, tetrahydrofurfuryl alcohol, diethyl tolumide, monoisopropylidene glycerine, sulfoxides, and similar chemicals such as but not limited to dimethylsulfoxide, dimethylacetamide, dimethylformamide, decylmethylsulfoxide, dimethylisosorbide, Caprylocaproyl polyoxyl-8 glycerides, triacetine, and combinations thereof.

Item 53. The transdermal patch according to any preceding item, wherein the solvent is selected from the group consisting of C1-C20 alcohols, polyhydric alcohols, isopropyl myristate, glycols selected from the group consisting of propylene glycol, polyethylene glycol, dipropylene glycol and hexylene glycol; glycerin, imidazolidinones, 1,3-dimethyl-2-imidazolidinone (DMI), pyrrolidones selected from the group consisting of N-methyl 2-pyrrolidone (NMP), 2-pyrrolidone; sulfoxides selected from the group consisting of dimethyl sulfoxide and decyl methyl sulfoxide; dimethyl isosorbide, mineral oils, vegetable oils, and carboxylic acids selected from the group consisting of acrylic acid, lactic acid and acetic acid.

Item 54. The transdermal patch according to any preceding item, wherein the surfactant is selected from the group consisting of an anionic surfactant, a cationic surfactant, a zwitterionic surfactant, a nonionic surfactant, sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids (polysorbate 20, 40, 60 and 80 (Tween)), kolliphor derivates (macrogol ester) sodium lauryl sulfate, sorbitan esters selected form the group consisting of sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate and sorbitan tri-isostearate, lecithin pharmaceutical acceptable salts thereof and combinations thereof.

Item 55. The transdermal patch according to any preceding item, wherein the crystallization inhibitor is selected from the group consisting of cellulose ethers, methyl cellulose ethers, cellulose, hydroxylated cellulose, methyl cellulose, and hydroxylated methyl cellulose, hydroxypropyl cellulose (HPC), hydroxyethyl cellulose (HEC), hydroxypropylmethyl cellulose (HPMC), copolymers of methacrylic acid, polyvinylpyrrolidone (PVP) and its derivatives; polyvinylpyrrolidone/vinyl acetate (PVP/VA) copolymer, dextrin derivatives; polyethylene glycol (PEG); polypropylene glycol (PPG), polyvinyl alcohol (PVA), poloxamers, gums selected from guar, locust, karaya, xanthan, gelatin, and derivatives thereof.

Item 56. The transdermal patch according to any preceding item, wherein the adhesive comprises a polymer based on acrylic acid and its esters, isobutylenes, ethylene-vinyl acetate copolymers, natural rubbers, synthetic rubbers, styrene-diene copolymers, styrene-butadiene block copolymers, isoprene block copolymers, acrylonitrile-butadiene rubber, butyl rubber and neoprene rubber, pressure sensitive adhesives based on silicone, hot-melt adhesive, mixtures of esters of hydrogenated colophony with cellulose derivatives, and combinations thereof.

Item 57. The transdermal patch according to any preceding item, wherein the adhesive comprises an acrylic-based polymer.

Item 58. The transdermal patch according to any preceding item, wherein the acrylic-based polymer contains more than 1% of the poly acrylic monomer.

Item 59. The transdermal patch according to any preceding item, having up to about 20% by weight of clobazam.

Item 60. The transdermal patch according to any preceding item, having a level of clobazam above 3% w/w.

Item 61. The transdermal patch according to any preceding item, which provides a flux rate of about 0.5 µg/cm$^2$·hr to about 20 µg/cm$^2$·hr for more than 24 hours.

Item 62. A method for treating or preventing epilepsy, anxiety, LGS or related disorders comprising the step of applying the transdermal patch of claim 1 to a subject in need thereof.

Item 63. The method according to any preceding item, wherein the transdermal patch is a pressure sensitive patch that is applied to the subject for more than 24 hours, 1-2 days, 2-3 days, 3-4 days, 4-5 days, or 5-7 days.

Item 64. The method according to any preceding item, wherein the subject achieves at least 10 ng/ml plasma concentration of clobazam after administration of the patch.

Item 65. The transdermal patch according to any preceding item, wherein the clobazam content of said patch remains substantially unchanged when stored at 40° C. for four weeks.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. Patents, patent applications, and publications are cited throughout this application, the disclosures of which, particularly, including all disclosed chemical structures, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed:

1. A transdermal patch comprising:
   a. 10 to 90% w/w of microemulsion phase;
   b. 0.1% to 40% w/w of adhesive;
   c. 0.1 to 10% w/w of a crystallization inhibitor;

d. a physiologically effective amount of clobazam loaded in the microemulsion phase, wherein the clobazam content of said patch remains substantially free of crystals when stored at 25° C. for at least four weeks;
e. a backing layer;
f. a drug-containing layer comprising the microemulsion phase, wherein the drug-containing layer is disposed on a body proximal side of the backing layer; and
g. a body-contacting adhesive layer and a rate-control layer, wherein the body-contacting adhesive layer and the rate-control layer are disposed on a body proximal side of the drug-containing layer and reduce a flux rate of the clobazam, and wherein the body-contacting adhesive layer and the rate-control layer are made of a material that is different from the drug-containing layer.

2. The transdermal patch of claim 1, wherein the microemulsion phase is an oil-in-water microemulsion comprising: (i) an oily phase comprising clobazam or a pharmaceutically acceptable salt thereof, an oily component and a solvent; (ii) a hydrophilic phase comprising a surfactant, and (iii) at least one permeation enhancer and/or a solubilizer.

3. The transdermal patch of claim 2, wherein the oily component comprises one or more oils selected from the group consisting of aromatic oils, mineral oils, plant oils, animal oils, synthetic oils, silicone oils, fluoro oils, and any combination thereof.

4. The transdermal patch of claim 2, wherein the oily phase further comprises one or more excipients selected from the group consisting of alkyl benzoates, carboxylic acids, surfactants, emulsifiers, ketone and alcohol functional group and any combination thereof.

5. The transdermal patch of claim 2, wherein the hydrophilic phase comprises at least one excipient selected from the group consisting of alcohol, ketone group, glycols, esters, and any combination thereof.

6. The transdermal patch of claim 2, wherein the permeation enhancer selected from the group consisting of aliphatic alcohols, fatty acids having chain of 4 to 20 carbons, fatty acid esters, alcohol amines, polyhydric alcohol alkyl ethers, polyoxyethylene alkyl ethers, glycerides, middle-chain fatty acid esters of polyhydric alcohols having chain of 8-20 carbon atoms, alkyl esters having chain of 1-6 carbon atoms, acylated amino acids, pyrrolidone, pyrrolidone derivatives, and ethoxylated fatty alcohols.

7. The transdermal patch of claim 2, wherein the solubilizer is selected from the group consisting of polysorbate, span, surfactants, propylene glycol monocaprylate and its derivatives, glycols and its derivatives, triglycerides and its derivatives, diethylene glycol monoethyl ether, cyclodextrins, polyhydric alcohol, polyethylene glycol, tetrahydrofurfuryl alcohol, diethyl tolumide, monoisopropylidene glycerine, sulfoxides, dimethylsulfoxide, dimethylacetamide, dimethylformamide, decylmethylsulfoxide, dimethylisosorbide, Caprylocaproyl polyoxyl-8 glycerides, triacetine, and combinations thereof.

8. The transdermal patch of claim 2, wherein the solvent is selected from the group consisting of C1-C20 alcohols, polyhydric alcohols, isopropyl myristate, glycols selected from the group consisting of propylene glycol, polyethylene glycol, dipropylene glycol and hexylene glycol; glycerin, imidazolidinones, 1,3-dimethyl-2-imidazolidinone (DMI), pyrrolidones selected from the group consisting of N-methyl 2-pyrrolidone (NMP), 2-pyrrolidone; sulfoxides selected from the group consisting of dimethyl sulfoxide and decyl methyl sulfoxide; dimethyl isosorbide, mineral oils, vegetable oils, and carboxylic acids selected from the group consisting of acrylic acid, lactic acid and acetic acid.

9. The transdermal patch of claim 2, wherein the surfactant is selected from the group consisting of an anionic surfactant, a cationic surfactant, a zwitterionic surfactant, a nonionic surfactant, sodium stearyl fumarate, diethanolamine cetyl sulfate, polyethylene glycol, isostearate, polyethoxylated castor oil, benzalkonium chloride, nonoxyl 10, octoxynol 9, polyoxyethylene sorbitan fatty acids selected from the group consisting of polysorbate 20, 40, 60 and 80, kolliphor derivates, sodium lauryl sulfate, sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate and sorbitan tri-isostearate, lecithin pharmaceutical acceptable salts thereof and combinations thereof.

10. The transdermal patch of claim 1, wherein the crystallization inhibitor is selected from the group consisting of cellulose ethers, methyl cellulose ethers, cellulose, hydroxylated cellulose, methyl cellulose, and hydroxylated methyl cellulose, hydroxypropyl cellulose (HPC), hydroxyethyl cellulose (HEC), hydroxypropylmethyl cellulose (HPMC), copolymers of methacrylic acid, polyvinylpyrrolidone (PVP) and its derivatives; polyvinylpyrrolidone/vinyl acetate (PVP/VA) copolymer, dextrin derivatives; polyethylene glycol (PEG); polypropylene glycol (PPG), polyvinyl alcohol (PVA), poloxamers, gums selected from guar, locust, karaya, xanthan, gelatin, and derivatives thereof.

11. The transdermal patch of claim 1, wherein the adhesive comprises a polymer based on acrylic acid and its esters, isobutylenes, ethylene-vinyl acetate copolymers, natural rubbers, synthetic rubbers, styrene-diene copolymers, styrene-butadiene block copolymers, isoprene block copolymers, acrylonitrile-butadiene rubber, butyl rubber and neoprene rubber, pressure sensitive adhesives based on silicone, hot-melt adhesive, mixtures of esters of hydrogenated colophony with cellulose derivatives, and combinations thereof.

12. The transdermal patch of claim 1, wherein the adhesive comprises an acrylic-based polymer.

13. The transdermal patch of claim 12, wherein the acrylic-based polymer contains more than 1% of the poly acrylic monomer.

14. The transdermal patch of claim 1, having up to about 20% by weight of clobazam.

15. The transdermal patch of claim 14, having a level of clobazam above 3% w/w.

16. The transdermal patch of claim 1, which provides a flux rate of about 0.5 µg/cm$^2$·hr to about 20 µg/cm$^2$·hr for more than 24 hours.

17. A method for treating or preventing epilepsy, anxiety, Lennox-Gastaut syndrome (LGS) or related disorders comprising the step of applying the transdermal patch of claim 1 to a subject in need thereof.

18. The method of claim 17, wherein the transdermal patch is a pressure sensitive patch that is applied to the subject for more than 24 hours, 1-2 days, 2-3 days, 3-4 days, 4-5 days, or 5-7 days.

19. The method of claim 17, wherein the subject achieves at least 10 ng/ml plasma concentration of clobazam after administration of the patch.

20. The transdermal patch of claim 1, wherein the clobazam content of said patch remains substantially unchanged when stored at 40° C. for four weeks.

* * * * *